US000001498H

United States Patent [19]

Murray et al.

[11] Patent Number: H1498

[45] Date of Patent: Nov. 7, 1995

[54] POLYGENIC TRAIT DETERMINANTS: MAIZE DWARF MOSAIC VIRUS

[76] Inventors: Michael G. Murray, 9 Grafton Cir., Madison, Wis. 53716; Jane H. Cramer, 4821 Woodburn Dr., Madison, Wis. 53711; Jeanne Romero-Severson, P.O. Box 157, Mazomainie, Wis. 53560; David West, 363 S. Warren, Prescott, Wis. 54021; Yu Ma, 4118 St. Clair St., Madison, Wis. 53711

[21] Appl. No.: 50,965

[22] Filed: Apr. 21, 1993

Related U.S. Application Data

[62] Division of Ser. No. 126,767, Nov. 30, 1987, abandoned.

[51] Int. Cl.[6] ..... A01H 1/00

[52] U.S. Cl. ..... 47/58; 47/DIG. 1; 435/172.3; 435/172.1

[58] Field of Search ..... 435/172.3, 172.1; 800/205; 526/23.1, 24.1, 24.2, 24.3, 23.6

OTHER PUBLICATIONS

Stuber et al. (1982) Crop Science vol. 22. pp. 737–740.
Helentjaris et al. (1985) Pl. Mol. Bio. vol. 5: 109–118.
Helentjaris et al. (1986) Tag. vol. 72: 761–769.
Atkins et al. (1942) J. Amer. Soc. Agron. 34:667–668.
Beckmann, J. S. and Soller, M. (1983) Theor. Appl. Genet. 67:35–43.
Burr, B. et al. (1983) in *Genetic Engineering Principles and Methods,* vol. 5, Setlow and Hollander (eds.), pp. 45–49.
Burr, B. and Burr, F. A. (1985) *Biotechnology in Plant Science,* M. Zaitlin et al. (eds.), Academic Press, Inc.
Edwards, M. D. et al. (1987) Genetics 116:113–125.
Ellis, T. H. N. (1986) Theor. Appl. Genet. 72:1–2.
Everson et al. (1955) Agron. J. 47:276–280.
Evola, S. V. et al. (1986) Theor. Appl. Genet. 71:765–771.
Furnival, G. M. and Wilson, Jr., R. W. (1974) Technometrics 16:499–511.
Helentjaris, T. et al. (1986) Proc. Natl. Acad. Sci. USA 83:o6035–6039.
Helentjaris, T. (1987) Trends Genet. 3:217–221.
Konstantinov, K. and Denic, M. (1985) Genetika 17(3):229–235.
Landry, S. S. and Michelmore, R. W. (1985) *Tailoring Genes for Crop Improvement,* G. Bruening et al. (eds.), pp. 25–44.
Nienhuis, J. et al. (1987) Crop Sci. 27:797–803.
Pereira et al. (1985) EMBO J. 4(1):17.
Rosenkranz, E. and Scott, G. E. (1984) Phytopathology 74:71–76.
Soller, M. and Beckmann, J. S. (1983) Theor. Appl. Genet. 67:25–33.
Sturtevant, A. H. (1913) J. Exp. Zool. 14:43.
Tanksley, S. D. et al. (1981) Theor. Appl. Genet. 60:291–296.

*Primary Examiner*—Shean Wu

[57] ABSTRACT

A set of nucleic acid probes useful for tracking Maize Dwarf Mosaic Virus Resistance (MDMV), a polygenic trait, is provided. Chromosome segments are identified enabling isolation of the genes governing this trait.

A general method for identifying probes useful for tracking and introgressing polygenic traits into elite genomes and identifying chromosome segments governing the traits is also provided. This method involves the analysis of RFLP polymorphisms between parent donor and recipient genotypes and observed phenotypic data using multiple regression by leaps and bounds ("leaps"), followed by standard multiple regression applied to the "leaps" data. The "leaps" data may be used to identify flanking markers, and epistasis may be determined by analysis of the multiple regression data.

Kits comprising a subset of the most useful probes (those most closely linked to the trait of interest) are provided. The kits may also comprise flanking probes. Flanking probes used in combination with the most closely linked probes are useful in identifying situations in which donor DNA tends to move in clumps and recovering rare individuals in which traits of interest have separated from surrounding donor DNA, so that elite recipient DNA may be maximized.

1 Claim, 13 Drawing Sheets

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

POLYGENIC TRAIT DETERMINANTS: MAIZE DWARF MOSAIC VIRUS

This is a divisional of application Ser. No. 07/126,767, filed Nov. 30, 1987 abandoned now.

FIELD OF THE INVENTION

This invention lies in the field of genetic engineering using recombinant nucleic acid markers, and specifically in the field of plant breeding.

BACKGROUND OF THE INVENTION

Genetic linkage has been studied and linkage maps have been developed for a wide variety of species, including plant species. Localization of genes of interest can be accomplished through linkage analysis with mapped markers as described by Patterson, E. B. (1982) "The mapping of genes by the use of chromosomal aberrations and multiple marker stocks", pp. 85–88, In: *Maize for Biological Research* (W. F. Sheridan, ed.) University Press, University of North Dakota, incorporated herein by reference.

The concept of using markers associated with favorable agronomic traits to track and recover the favorable traits in segregating populations is known to the art, e.g. Atkins et al. (1942), "The isolation of isogenic lines as a means of measuring the effects of awns and other characters in small grains," J. Amer Soc Agron 34:667–668; Everson, et al. (1955), "The genetics of yield differences associated with awn barbing in the barley hybrid (Lion×Atlas)× Atlas," Agron. J. 47:276–280; Carol Rivin et al. (1983) "Evaluation of Genomic Variability at the Nucleic Acid Level," Plant Mol. Biol. Reporter Vol. 1, p. 9; Helentjaris, T. G., PCT Application published Dec. 6, 1984, "Process for genetic mapping and cross-breeding thereon for plants".

Such genetic linkage has been invaluable in the introgression of specific chromosomes or chromosome segments into various genetic backgrounds (Rick, C. M. and Khush, G. S. (1969) "Cytogenic explorations in the maize genome", pp. 45–68, In: *Genetics Lectures* Vol. I (R. Bogart, ed.), Oregon State University Press, Corvalis; and C. Rhyne (1960) "Linkage studies in Gossypium II altered recombination values in linkage group of allotetraploid *G. hirsutum* L. as a result of transferred diploid species genes" Genetics 45:673–683). The use of genetic markers speeds the transfer of a specific locus to a desirable genotype. In plant breeding, tissue of young plants can be tested for the presence of marker alleles linked to the desirable trait and only individuals displaying the presence of such marker alleles need be grown to adulthood, transplanted and used to produce progeny, thus eliminating many time-consuming steps required in traditional plant breeding. For example, the tomato nematode resistance gene, mi has been successfully transferred though linkage with an acid phosphatase isozyme marker (Tanksley, S. D. et al. "Use of an Acid Phosphatase Isozyme for Predictive Association with an Agronomic Trait," Plant Mol. Biol. Rep., In press). Such markers are also useful in facilitating the recovery of a desired recurrent parent in a backcrossing program (e.g. S. D. Tanksley, H. Medina-Filho and C. M. Rick (1981) "The effect of isozyme selection on metric characters in an interspecific backcross of tomato-basis of an early screening procedure" Theor. Appl. Genet. 60:291–296).

Molecular markers such as isoenzyme, protein and nucleic acid markers, the variants of which do not often have any noticeable effect on phenotype are preferred over the phenotypic markers used in classical breeding methods. See Newton, K. J. et al. (1980) "Genetic basis of the major malate dehydrogenase isozymes in maize," Genetics 95:424–442; Goodman, M. M. et al. "Maize", Isozymes in Plant Genetics and Breeding, Part B (Tanksley, S. D. et al. eds.) (1983) Elsevier Science Publishers.

Nucleic acid markers provide certain advantages over isozyme and protein markers. With DNA markers, allelic variation is detected by first digesting DNA from the individuals being analyzed with a variety of restriction endonucleases. The resulting fragments are separated by electrophoresis and transferred to solid support matrices. Allelic fragments are then identified by hybridizing the DNA on the supports to cloned, radioactively-labelled, homologous sequences. Genetic variation detected in this manner has often been referred to as restriction fragment length polymorphism (RFLP). The number of RFLP's are virtually unlimited. They are unlikely to have an effect on phenotype, are codominant and are inherited in a predictable fashion.

A theoretical discussion applying known methods of genetic mapping to RFLP's and practical applications thereof is given in Beckmann, J. S. and Soller, M. (1983), "Restriction fragment length polymorphisms in genetic improvement: methodologies, mapping and costs", Theor. and Appl. Genetics 67:35–43; and Soller, M. and Beckmann, J. S. (1983), "Genetic polymorphism in varietal identification and genetic improvement," Theor. and Appl. Genetics 67:25–33, both of which are incorporated herein by reference. See also Burr, B., Evola, S. D., Burr, F. A. and Beckmann, J. S. (1983), "The application of restriction fragment length polymorphisms to plant breeding", Genetic Engineering Principles and Methods, (Setlow and Hollander, eds.) Vol. 5:45–49, also incorporated herein by reference, and Ellis, T. H. N. (1986) "Restriction Fragment Length Polymorphism Markers in Relation to Quantitative Characters", Theor. Appl. Genet. 72:1–2. The usefulness of RFLP mapping for maize also has been discussed by S. V. Evola et al. (1986) "The suitability of restriction fragment length polymorphisms as genetic markers in maize", Theor. Appl. Genet. 71:765–771. No specific map positions for any DNA probes are discussed in any of the above articles.

Map positions for many cloned DNA sequences have been reported in connection with maize (*Zea mays*) Helentjaris, T. et al. (1986) "Use of monosomics to map cloned DNA fragments in maize", Proc. Natl. Acad. Sci. USA 83:6035–6039. This article reports the identification of 112 loci using RFLP's. The fragments mapped by Helentjaris et al. are defined relative to their relationship to certain previously-mapped markers, and relative to each other. This article is incorporated herein by reference. Other mapping efforts are currently in progress throughout the industry and the maize genome is rapidly becoming saturated with mapped molecular markers which are freely available to the public.

While nucleic acid (RFLP) markers have been used to locate and manipulate traits determined by single genes, they have not been successfully used to locate and manipulate traits determined by more than one gene. Burr, B. and Burr, F. A. (1985), "Toward a Molecular Characterization of Multiple Factor Inheritance," Biotech. in Plant Sci. (Zaitlin, M. et al. eds.) discusses this concept in general with respect to quantitative traits without providing specific enablement. Landry, B. S. and Michelmore, R. W. (1985), "Methods and Applications of Restriction Fragment Length Polymorphism Analysis to Plants," Tailoring Genes for Crop Improvement (Bruening G., et al. eds.) 25–44 is a general review article containing a section discussing the use of molecular markers to track and manipulate quantitative trait loci, but without providing enabling disclosure.

A disadvantage in the use of molecular markers for tracking and breeding traits is the fact that cross-overs occurring in progeny predictably will separate the trait of interest from the linked marker used to track it in a certain percentage of individuals. Nuinhaus, J. et al. (1987), "Restriction Fragment Length Polymorphism Analysis of Loci Associated with Insect Resistance in Tomato," Crop Sci. 27:797–803.

Another disadvantage of prior methods for tracking traits using molecular markers is the fact that a particular linked marker allele may not invariably correlate with the presence of the phenotype being studied. Many phenotypes are developmentally expressed, and unless the populations are scored at multiple times during their life cycles, important associated marker alleles can fail to be identified.

Helentjaris, T. (1987), "A genetic linkage map for maize based on RFLPs," Trends in Genetics 3:217–221 provides a maize linkage map and several loci for plant height determinants with the relative contribution of each loci to the phenotype indicated. No enabling method for determining such loci is provided, however. Edwards, M. D., et al. (1987), "Molecular-Marker-Facilitated Investigations of Quantitative-Trait Loci in Maize. I. Numbers, Genomic Distribution and Types of Gene Action," Genetics 116:113–125, provide a method for locating quantitative trait loci using molecular markers. In this method, single-factor analysis is used to determine loci associated with a number of different traits. This analysis was followed by a multiple regression method to determine the relative contribution of each such locus to the given trait. This method, while identifying loci determining polygenic traits and the relative contribution of each, has the drawback of failing to provide a method for ensuring against loss of the trait being tracked due to cross-over in progeny populations. The method described above also fails to take into account the possibility of developmentally-expressed phenotypes.

Nienhuis, J. et al. (1987), "Restriction Fragment Length Polymorphism Analysis of Loci Associated with Insect Resistance in Tomato," Crop Sci. 27:797–803 discloses the use of RFLP technology to identify quantitative trait loci affecting expression of insect resistance in a wild tomato species. Conventional linkage analysis was used to locate RFLP loci associated with the trait, followed by linear and multiple regression to determine the relative contribution of each locus. Analysis of the residual plots indicated that one or more additional loci with major effects had not been identified. The article suggests the use of flanking markers to localize a target quantitative trait locus, but characterizes this as "problematic."

No previously described method for locating DNA governing polygenic traits has been successfully used to introgress such traits into a second or elite genotype.

The present application provides a method for tracking and manipulating polygenic traits in a breeding program which solves the problem of loss of the trait due to cross-over in the progeny population. This method involves the analysis of molecular marker linkage data for a predetermined polygenic trait by the method of multiple regression by leaps and bounds (Furnival, G. M. and Wilson, Jr., R. W. (1974) "Regression by leaps and bounds," Technometrics 16:499–511). This method was developed to assess the relative contributions of causative factors on effects, (i.e. numerous independent factors on dependent variables), and has not previously been applied to genetic analysis, possibly because of lack of appreciation by those skilled in the art of the possibility of making an analogy between such classical causative factors and marker alleles.

The method of the present application also ensures that marker alleles corresponding to developmentally expressed phenotypes are identified.

The method of the present application is exemplified by the identification of loci determining maize dwarf mosaic virus (MDMV) resistance in maize. Maize dwarf mosaic virus occurs throughout the United States and Europe. Resistant cultivars of dent corn have been developed, but sufficient genetic loci determining such resistance to enable introgression of the trait into a variety lacking such resistance have not been previously identified. In an abstract for a presentation to the 78th Annual Meeting of the American Society of Agronomy at New Orleans, Louisiana Nov. 30 through Dec. 5, 1986, G. E. Scott reports the linkage of MDMV resistance to endosperm color in corn, concluding that one or more genes for resistance must be located on the long arm of chromosome 6. The abstract does not provide an enabling disclosure nor locate the gene or genes with sufficient exactitude to enable their isolation. Resistant cultivars of sweet corn having quality factors acceptable to the industry have not been developed, leading to serious economic losses in the United States due to MDMV. Use of identified loci for MDMV resistance is thus useful for producing inbred cultivars of resistant sweet corn.

Inheritance of resistance to MDMV is not clearly understood. The number of genes which contribute to resistance and the nature of gene action appears to be significantly dependent upon the source of MDMV resistance, the susceptible inbreds, the time of scoring, and the method of inoculum production and application. (Louie, R. (1986), "Effects of genotype and inoculation protocols on resistance evaluation of maize to maize dwarf mosaic virus strains," Phytopathology 76:769–773 .

Roane et al. (1983), "Inheritance of resistance to maize dwarf mosaic virus in maize inbred line Oh7B," Phytopathology 73:845–850, reported that in crosses between the resistant line Oh47b and two susceptible lines, Oh43 and Pa91, the inheritance of resistance was conditioned by one dominant gene. Rosenkranz, E. and Scott, G. E. (1984), "Determination of the number of genes for resistance to maize dwarf mosaic virus strain A in five corn inbred lines," Phytopathology 74:71–76, showed that the inbreds Ga203, Ar254, and Pa405 appear to have three, two and five additive resistance genes respectively. Crosses in which the resistant lines B68 or Pa405 were the donors, and susceptible sweet corns were the recipients revealed three genes, one of which must be present with the other two (Mikel, M. A. et al. (1984), "Genetics of resistance of two dent corn inbreds to maize dwarf mosaic virus and transfer of resistance into sweet corn," Phytopathology 74:467.

The difficulty of assessing genotype from phenotype, and the existence of as many as five significant genes make MDMV resistance an ideal problem for the application of RFLP technology. A further difficulty is provided by the fact that genomic material of resistant MDMV inbred lines tends to move in large segments. This makes it difficult to maximize the presence of genes governing the desired trait from the donor parent while minimizing the presence of surrounding, less desirable DNA. This problem is not specific to MDMV, but is a common problem which is difficult to identify and deal with not only in maize but in the selective breeding of other species as well. The present invention involves the identification of chromosome regions which are associated with MDMV resistance, the prediction of which progeny in an advanced generation will be resistant and which not, and the assessment of recovery of the elite genotype. Rates of convergence upon the desired genotype are significantly increased while risk of losing essential marker loci is substantially reduced.

SUMMARY OF THE INVENTION

A set of primary probes or clones are provided linked with genes determining maize dwarf mosaic virus resistance or susceptibility. In the preferred embodiment, the probes are DNA probes having sequences hybridizable to portions of the maize genome close to (having at most about 10% recombination) with the genes of interest. These preferred clones are designated r179, c587, c512, c926, c329, gp144, r262 and r92. A library containing these probes in plasmids is on deposit according to Budapest Treaty requirements at the In Vitro International Depository of 611P Hammonds Ferry Road, Linthicum, Maryland 21090 deposited Nov. 30, 1987, entitled "Corn (Zea mays) Nuclear DNA Clones," under Accession No. IVI-10150.

A further set of flanking probes are provided to enable detection of a segment of genomic DNA known to contain the gene governing MDMV resistance. When an individual shows marker alleles corresponding to the parent donating the trait at both the locus of the primary probes and the flanking probes, it is known that the individual has the gene in question since the marker probe is selected such that the gene lies between the primary and the flanking loci or between two flanking loci on either side of the gene. When an individual shows marker alleles corresponding to the parent donating the trait at the locus of the primary probes and not the flanking probes, and still shows the phenotype associated with the locus, it is known that the individual has the desired gene, with minimal extraneous DNA from the donor parent. Use of these flanking probes enables the breeder to detect situations in which genomic material from the donor parent is moving in large segments, to identify the rare occurrence of individuals in which such large segments have not been transferred, and to maximize the presence of the elite DNA from the recipient parent.

A "flanking locus" as used herein, means a locus determined by the statistical methods described herein to have the second largest contribution to phenotypic variability among a set of linked probes. The "primary locus" is the locus having the largest contribution of the set of linked probes.

The flanking probes are designated r250, r271, gp53, gp52, r189, r21 and c595. These probes are on deposit with In Vitro International as part of the clone library referred to above.

The terms "clone" and "probe" are used interchangeably herein to refer to a nucleic acid fragment containing a sequence which is substantially homologous (preferably at least about 85% homologous) to a genomic DNA sequence and capable of hybridizing to a said genomic DNA sequence. A "clone" or "probe" may contain more or less nucleic acid than the restriction fragment to which it hybridizes. "Clone" or "probe" as used herein may refer to a linearized plasmid containing the nucleic acid fragment corresponding to a genomic DNA sequence, or to a fragment including extraneous sequences, such as tails and vector sequences, so long as it hybridizes to the genomic DNA.

The terms "trait", "characteristic", and "phenotype" are used interchangeably herein. A "trait" can be a classical phenotype such as the maize phenotypes, maize dwarf mosaic virus (MDMV) resistance, japonica, crinkly leaves, dwarf plant, etc., an enzymatic factor, or the characteristic of showing a particular restriction fragment length polymorphism when the DNA is digested with a particular restriction enzyme and probed with a particular clone. The latter is sometimes specifically referred to as a "marker allele."

The term "marker" refers to a genetic element (DNA governing a trait) which has been mapped, or for which recombination frequencies with other genetic elements have been determined. A "marker" can be any trait whose relationships with other markers are known. Isozyme markers know to the art such as idh2, enp1, and mdh1 are useful in the practice of this invention. "Marker clones" or "DNA, RNA or RFLP markers" are clones of this invention or a nucleic acid fragment whose loci on chromosomes or linkage groups have previously been determined.

A "locus" is a site on the genome corresponding to an observable trait. In the case of an RFLP trait, the locus (or loci) are DNA sequences which hybridize to a particular clone or probe.

"MDMV resistance" defining a trait is used to mean both MDMV resistance and MDMV susceptibility since the trait itself includes both ends of the spectrum. The statistical methods described herein refer to a scoring method for this trait in which higher numbers indicate susceptibility, or observable presence of the disease, and lower numbers indicate resistance, or relative absence of the disease.

DNA fragments comprising DNA sequences governing MDMV resistance are also provided. These fragments may be isolated and sequenced by means known to the art, and are the segments of the genome falling between flanking and primary markers or between flanking markers. For purposes of this invention, it is not necessary to identify the chromosome on which each segment occurs, however, this information is provided as a matter of general information. The numbers in parentheses below refer to map distances between the markers, or more accurately, recombination frequencies between the markers. These numbers may vary from cultivar to cultivar, and are not part of the essential definition of the DNA fragments. The DNA fragments of this invention are:

Chromosome 1: c587 (15.4) c512 (3.8) r250. Alternatively, only the segment c512–r250 may be used.

Chromosome 3: r179 (8.7) r271.

Chromosome 5: c926 (5.4) gp53.

Chromosome 5: c329 (9.8) gp52.

Chromosome 6: gp144 (10.4) r189.

Chromosome 8: r262 ( 11.1 ) r21.

Chromosome 9: c595 (1.6) r92. Alternatively, the fragment on Chromosome 9 may defined as the segment of Chromosome 9 lying between markers on either side of c595 and having a percent recombination rate with c595 of no more than about ten.

The probes and DNA fragments of this invention may be used to develop additional or substitute probes mapping to the same or contiguous regions. For example, any other phage or plasmid clone (or subclone thereof) which hybridizes to a clone of this invention is a substitute clone. Nucleic acid hybridization conditions may be employed by those skilled in the art utilizing well-known, published equations, for example as described in Nucleic Acid Hybridization: A Practical Approach, (Hames, B. D. and Higgins, S. J., eds.) (1985), IRL Press, Oxford. To maximize accuracy of results, it is preferred that the hybridization stringency be such that sequences which are less than about 85% homologous will not hybridize. Any new probe or DNA fragment which is identified using a probe or fragment of this invention is an equivalent to the probe or fragment of this invention.

Both DNA and RNA versions of the probes and fragments are covered by this invention. RNA probes and fragments may be transcribed or synthesized using means known to the art once DNA versions of the probes and fragments have been developed.

Equivalent probes or markers may be used to define chromosome segments comprising DNA governing MDMV resistance, and chromosome segments so defined are equivalent to the chromosome segments defined by the probes named herein and are within the scope of this invention.

The probes may be usefully combined into kits useful to plant geneticists for manipulating the MDMV resistance trait. An essential probe is r179. This probe is essential for the expression of resistance (i.e., it is epistatic to each of the following probes. The genomic DNA fragment, r179–r271 contains the actual gene governing the trait at this locus. The kit therefore should contain probes r179 and flanking probe r271.

A kit additionally comprising the primary probe gp144 with or without its associated flanking marker, r189, defining DNA segment gp144–r189 will be useful to account for about 37–41% of the phenotypic variability, provided that the B68 alleles of r179 alone or in combination with its flanking marker r271 are present.

The further addition of primary probe c512, with or without its associated flanking probe r250, defining DNA segment c512–r250, or the second linked probe, c587, defining DNA segment c587–r250, will account for up to about 79–84% of the phenotypic variability, provided that the B68 alleles of r179 alone or in combination with its flanking marker r271 are present and the B68 alleles for gp144 alone or in combination with its flanking marker r189 are present.

As the remaining probes are added, each will contribute an approximately equal further degree of predictability. These remaining probes, which may be added individually or separately, are c926, with or without its associated flanking probe, gp53, defining DNA segment c926–gp 53; c329, with or without its associated flanking probe, gp52, defining DNA segment c329–gp52; r262 with or without its associated flanking probe, r21, defining DNA segment r262–r21; and r92, with or without its associated flanking probe, c595, defining DNA segment c595–r92.

The probe r92 has two loci on the maize genome, on chromosome 1 and chromosome 9. To ensure that the correct locus is identified, the band size associated with r92 may be ascertained by determining linkage with c595, and the appropriate band size followed, as known to the art.

The methods described herein may be used to locate additional probes at additional loci with lesser contributions to the phenotype in the cultivars studied, or with greater or lesser contributions in other cultivars. Kits comprising such additional probes, alone or in combination with the probes described herein, are included within the scope of this invention. Preferably a kit for a given set of cultivars contains the primary and more preferably also the flanking probes associated with loci having the most effect on the phenotype. Additional probes for loci having lesser effect on the phenotype may be added as economic feasibility dictates.

A generalized method for identifying a heritable association between nucleic acid marker probes and a polygenic phenotype not limited to maize is provided. A "polygenic" trait is a trait controlled by multiple genetic loci. Preferably, at least about 80% of the trait is governed by no more than about four loci, as the fewer loci required to manipulate the trait in a breeding program, the more convenient and economically feasible such manipulation will be. Quantitative traits such as height and yield are often polygenic traits, but are not necessarily so. The preferred embodiment for this method exemplified herein involves maize. This method comprises:

(a) Analyzing DNA from a first parent having said phenotype and a second parent not having said phenotype by RFLP analysis to determine a set of sufficient nucleic acid marker probes which show different RFLP marker alleles in the two parents to cover a significant portion of the genome of the species. Preferably, probes are selected from a previously mapped genome at evenly spaced intervals along the genome, preferably at least one probe per chromosome or chromosome arm is selected, and more preferably, probes are selected at more or less regular intervals preferably of about 10 to about 20 map units. Markers other than RFLP probes may be used in this analysis, however, RFLP probes are preferred. As discussed above, the maize genome has been mapped with publicly available clones and other markers which may be used for this purpose. It is not necessary, however, that the genome be mapped or locations of the probes be previously selected. It is possible to develop a set of random clones, as is known to the art, for use in this invention without knowing map locations, chromosome locations, or even how many chromosomes the organism possesses.

As is known to the art, RFLP's may be developed using one or more restriction enzymes to cut the genomes being studied. Preferably, only one restriction enzyme is used. In the preferred embodiment this enzyme is EcoRI.

(b) Crossing said parents to obtain a progeny population of individuals which are segregating for said phenotype and selecting and scoring a statistically significant number of segregating individuals for the percent presence of said phenotype. Preferably, both the incidence of the phenotype in the population is scored and the severity is rated in each individual. More preferably, scoring is done at several times during the life cycle of the individuals so that developmentally occurring phenotypes can be associated with marker alleles.

(c) Analyzing DNA from said selected individuals to determine which parental marker alleles are present in each individual. This analysis is done by means known to the art, and is discussed in more detail hereinafter.

(d) Analyzing the data of steps (b) and (c) by multiple regression by leaps and bounds ("leaps") to determine a subset comprising a minimum number of primary marker alleles, preferably RFLP marker alleles, correlated with a maximum percent presence of said phenotype. This method is known to the art as described above, but has not previously been applied to genetic analysis. Preferably, phenotype severity data is included in this analysis as well, and more preferably, data from several ratings for each individual taken at two or more times in the life cycle of the individual are also used. Preferably, the data generated in this analysis are further analyzed to determine flanking markers, by examining the successive sets of marker loci chosen by "leaps" for those associated with the trait at each locus, but not as closely as the primary alleles. The "leaps" analysis will confirm that the trait is, in fact, polygenic.

The method preferably continues with an analysis of said subset by multiple regression, a method known to the art, to determine the relative contribution of each primary marker allele to the phenotype. This is important to the accuracy of the predictive value of the loci developed. For example, in the preferred embodiment described herein, several loci which were consistently picked by the "leaps" analysis did not contribute as highly to the trait as the loci defined by the claimed probes.

The multiple regression analysis determines what percent of the trait has been accounted for by the identified loci. The method also makes it possible to rank loci according to their contribution to the presence of the trait. It is desirable for efficiency of use in breeding that a minimum number of loci having a maximum effect on the trait be identified and used.

In addition, the multiple regression data makes it possible to determine epistatic effects of particular loci by preparing a normal quantile quantile plot of the multiple regression data. If the graph of observed deviation of the data from the straight line assumed by the method itself deviates from a straight line, indicating that the trait is actually more pronounced or severe than predicted at the high end and less pronounced or severe than predicted at the low end, epistasis is indicated. Graphing of the multiple regression data visually demonstrates such epistasis. In the preferred embodiment described below, for example, the r179 locus was shown to be epistatic to other loci, e.g. those at c512 and gp144.

The loci determined by the above method need not be located on a chromosome map of the species being tested, but are preferably so located to facilitate selection and use of equivalent probes and chromosome segments.

As will be appreciated by those skilled in the art, the method may be applied using additional primary and flanking markers to maximize association of the markers with the trait and determine the exact location of the genes governing the trait with sufficient accuracy to enable their isolation and sequencing.

The use of the RFLP probes described and claimed herein as linked with MDMV resistance enables the identification of loci governing MDMV resistance in any maize genome including both sweet and field corn varieties. The primary probes r179, gp144, and c512 are the most useful, although all the probes described above may be profitably used for this purpose.

The method, as applied to MDMV resistance in maize is useful for manipulation of the trait in sweet corn, for which no economically valuable resistant cultivars have previously been developed.

A method is also provided for transferring a desired polygenic phenotype, preferably MDMV resistance in maize from a donor genotype, preferably an MDMV resistant maize cultivar such as B68 into a recipient genotype, preferably an elite maize cultivar such as B73, comprising:

(a) determining the marker allele profiles of said donor and recipient genotypes having marker alleles substantially evenly distributed throughout the genome of said genotypes, as discussed above;

(b) identifying a minimum number of primary markers, preferably nucleic acid marker probes, showing marker alleles corresponding to a maximum presence of said phenotype in a progeny population obtained from crossing said donor and recipient genotypes by multiple regression by leaps and bounds and selecting a useful subset of those having the maximum individual contribution to aid presence of said phenotype by multiple regression, all as discussed above. Preferably, not only the presence of said phenotype in said population is correlated with marker alleles, but also the severity of the phenotype is rated, and preferably at different times during the life cycle of individuals being rated, and all rated factors are considered in a single factor whose correspondence with the RFLP marker alleles is determined. Preferably, flanking markers are also determined as discussed above.

(c) backcrossing individuals from said progeny population having marker alleles corresponding to said desired phenotype and otherwise having a maximum number of said useful subset of marker alleles of step (b) corresponding to said recipient genotype with parents of the recipient genotype to produce a first backcross population;

(d) backcrossing individuals from said first backcross population having marker alleles corresponding to said desired phenotype and otherwise having a maximum number of said useful subset of marker alleles of step (b) corresponding to said recipient genotype with parents of the recipient genotype to produce second and subsequent backcross populations until a last population having the desired similarity to the recipient genotype is achieved;

(e) selfing individuals of said last population and identifying those having marker alleles homozygous for said desired phenotype.

Preferably selection of individuals for crossing and, backcrossing is done by RFLP analysis in which both primary and flanking nucleic acid probes are used to identify and select individuals having the marker alleles shown by said probes corresponding to the donor phenotype. Individuals having said primary marker alleles corresponding to said donor genotype but having flanking marker alleles corresponding to said recipient genotype are tested for said phenotype by observation and individuals exhibiting the desired phenotype are selected as having maximum recipient DNA and minimal donor DNA other than DNA determining the desired phenotype. This method is especially valuable in cases where DNA from the donor genotype tends to move in larger than normal segments, as occurs with B68, a donor for MDMV resistance. Individuals having primary marker alleles corresponding to the donor genotype and flanking marker alleles corresponding to the recipient genotype are much more rare than classical Mendelian segregation would predict when segments of the donor genome tend to move in clumps. Identification of such rare genotypes prior to breeding in a greenhouse setting will greatly facilitate the breeding process.

BRIEF DESCRIPTION OF THE FIGURES

FIG. 1 is a bar chart comparing the effects of the number of B68 (MDMV resistant) alleles at marker loci r179 and gp144 on MDMV incidence to illustrate interaction between said loci.

FIG. 2 is a bar chart comparing the effects of the number of B68 (MDMV resistant) alleles at marker loci r179 and c926 on MDMV incidence to illustrate interaction between said loci.

FIG. 3 is a bar chart comparing the effects of the number of B68 (MDMV resistant) alleles at marker loci r179 and c329 on MDMV incidence to illustrate interaction between said loci.

FIG. 4 is a bar chart comparing the effects of the number of B68 (MDMV resistant) alleles at marker loci r179 and c512 on MDMV incidence to illustrate interaction between said loci.

FIG. 5 is a bar chart comparing the effects of the number of B68 (MDMV resistant) alleles at marker loci r179 and c262 on MDMV incidence to illustrate interaction between said loci.

FIG. 6 is a bar chart comparing the effects of the number of B68 (MDMV resistant) alleles at marker loci r179 and c587 on MDMV incidence to illustrate interaction between said loci.

FIG. 7 is a bar chart comparing the effects of the number of B68 (MDMV resistant) alleles at marker loci r179 and r92b on MDMV incidence to illustrate interaction between said loci.

In FIGS. 8–11, "4 B68 alleles" means the loci at both ends of the segment are homozygous for B68. "2 B68 alleles" means both loci defining the segment are heterozygous. "0 B68 alleles" means both the loci at both ends of the segment are homozygous for B73 alleles.

FIG. 8 is a bar chart comparing the effects on MDMV incidence of the number of B68 (MDMV resistant) alleles in chromosome segments A–A1 defined by marker loci r179 and r271 and B–B1 defined by marker loci gp144 and r189 to illustrate interaction between said segments.

FIG. 9 is a bar chart comparing the effects on MDMV incidence×severity of the number of B68 (MDMV resistant) alleles in chromosome segments A–A1 defined by marker loci r179 and r271 and B–B1 defined by marker loci gp144 and r189 to illustrate interaction between said segments.

FIG. 10 is a bar chart comparing the effects on MDMV incidence of the number of B68 (MDMV resistant) alleles in chromosome segments A–A1 defined by marker loci r179 and r271 and C–C1 defined by marker loci c512 and r250 to illustrate interaction between said segments.

FIG. 11 is a bar chart comparing the effects on MDMV incidence×severity of the number of B68 (MDMV resistant) alleles in chromosome segments A–A1 defined by marker loci r179 and r271 and C–C1 defined by marker loci c512 and r250 to illustrate interaction between said segments.

DETAILED DESCRIPTION OF THE PREFERRED EMBODIMENTS

Figure 1:
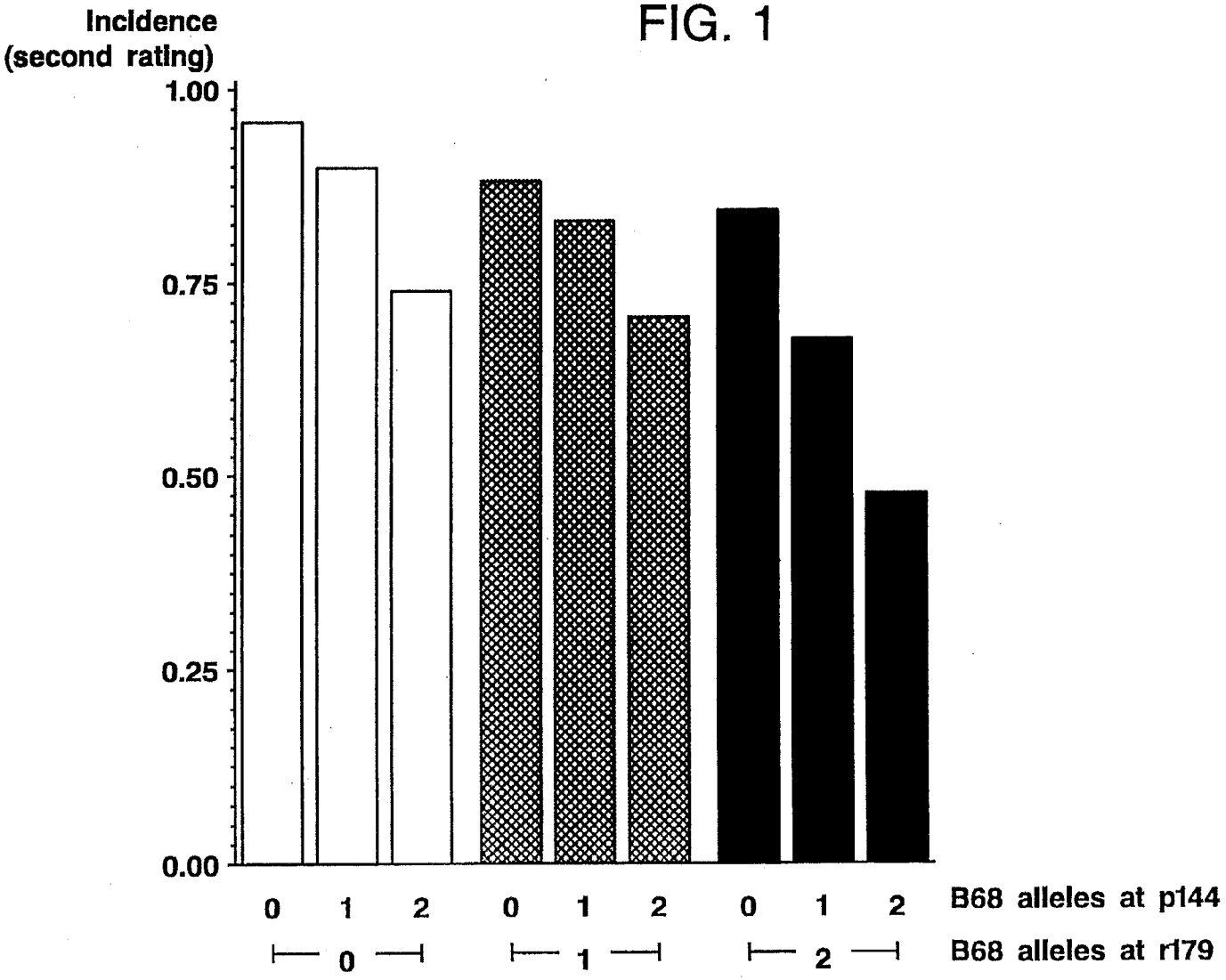
FIGS. 1–11 are bar charts showing the effect of marker loci on MDMV resistance. B68 alleles are alleles from the MDMV resistant donor-parent.
Figure 2:
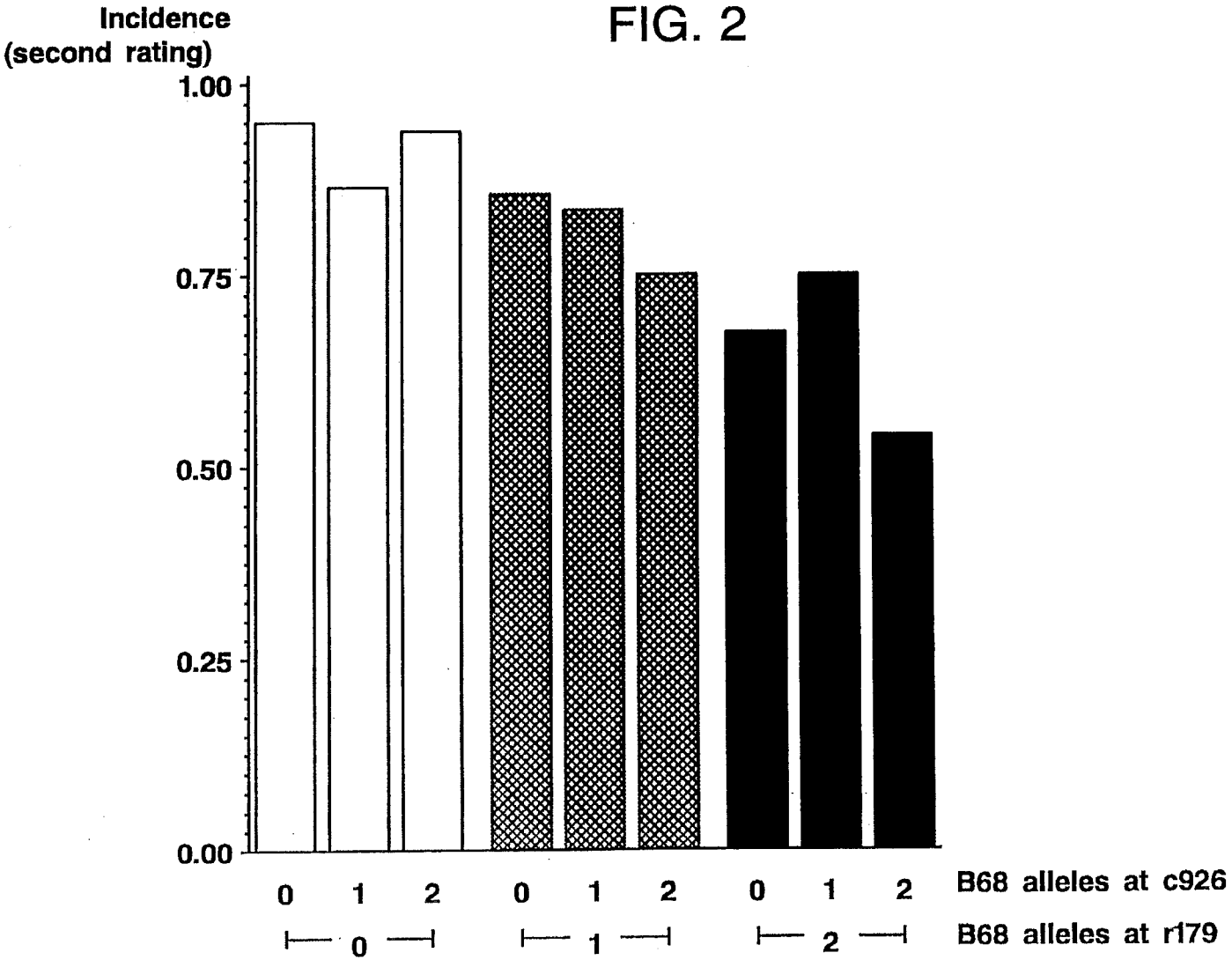
Figure 3:
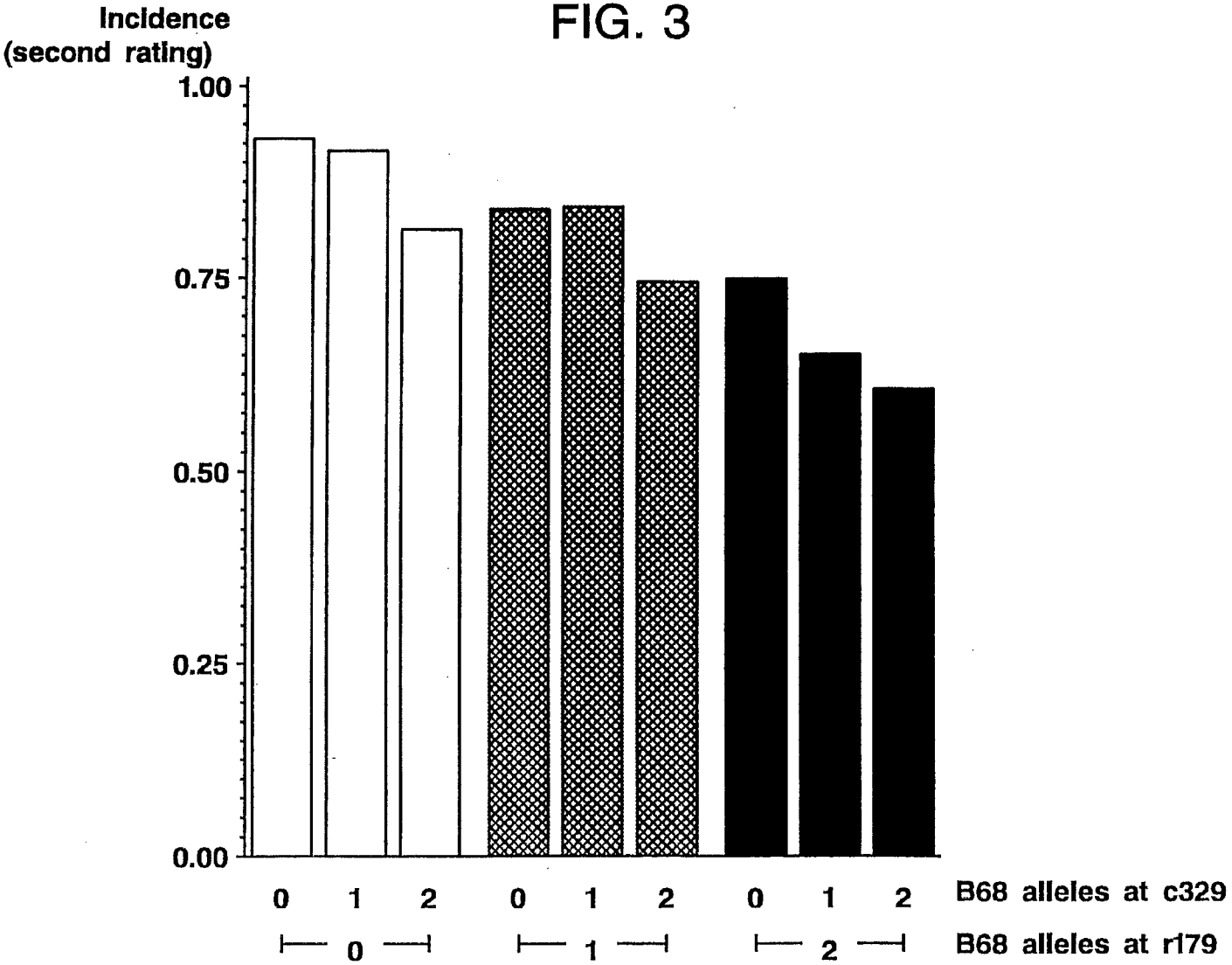
Figure 4:
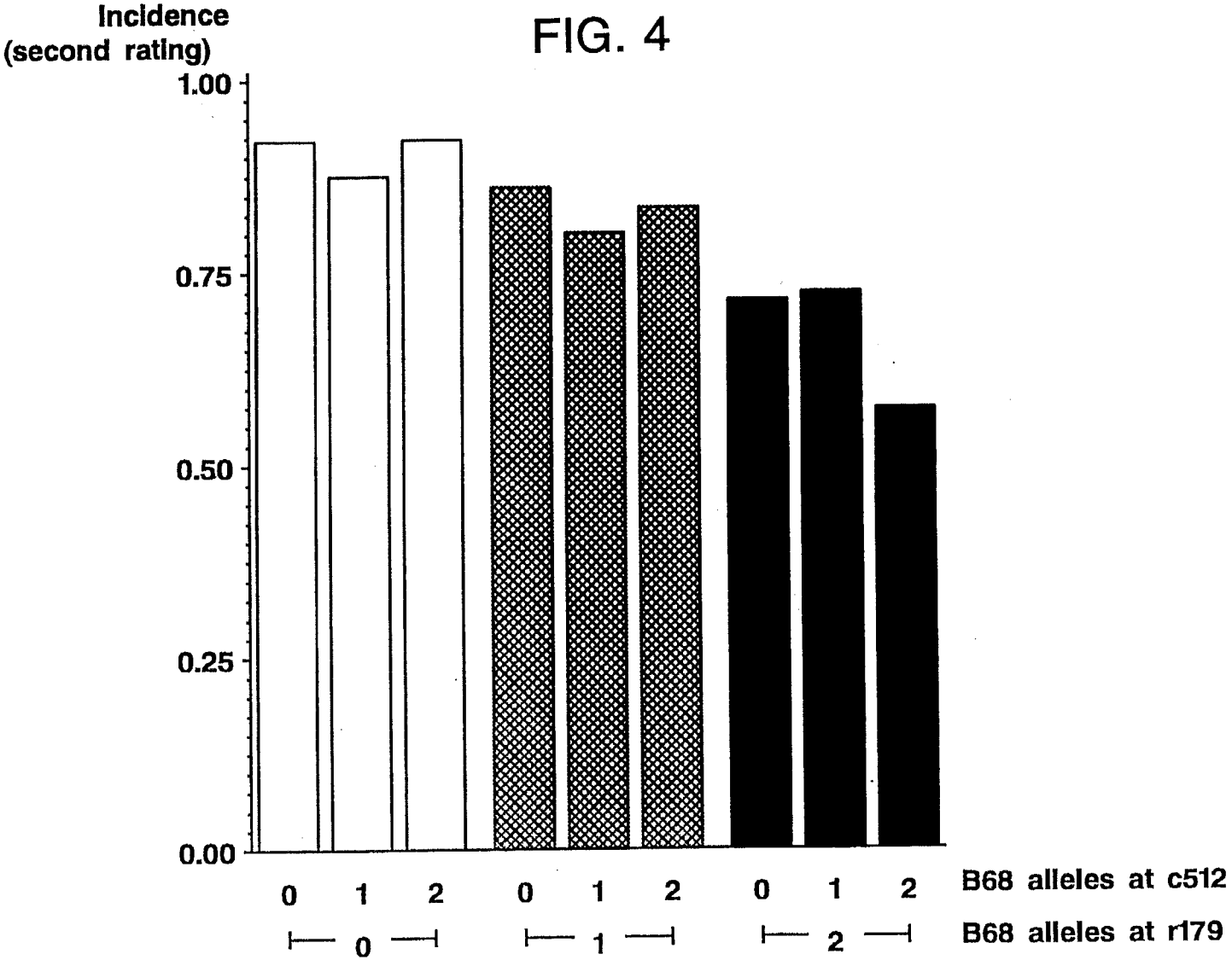
Figure 5:
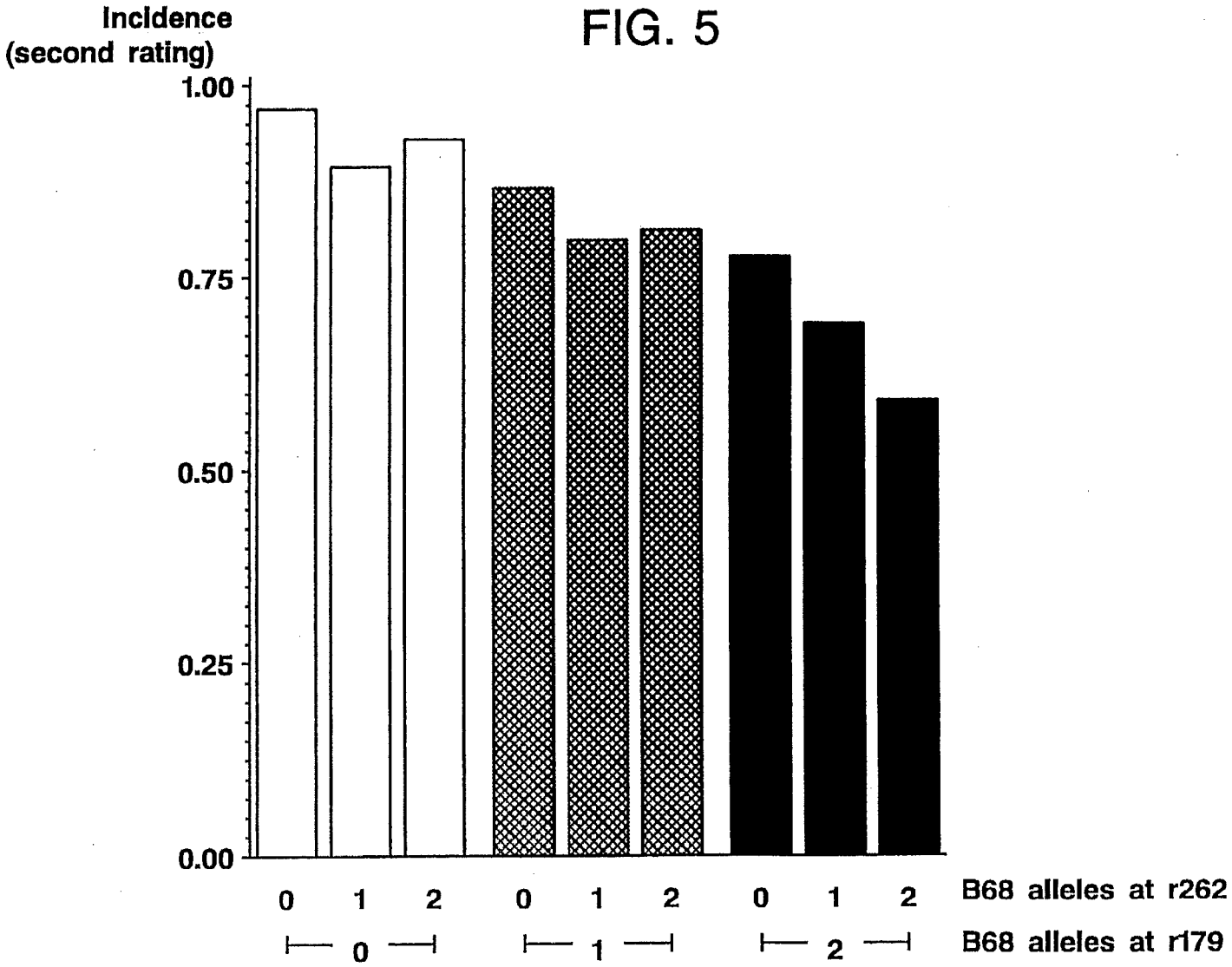
Figure 6:
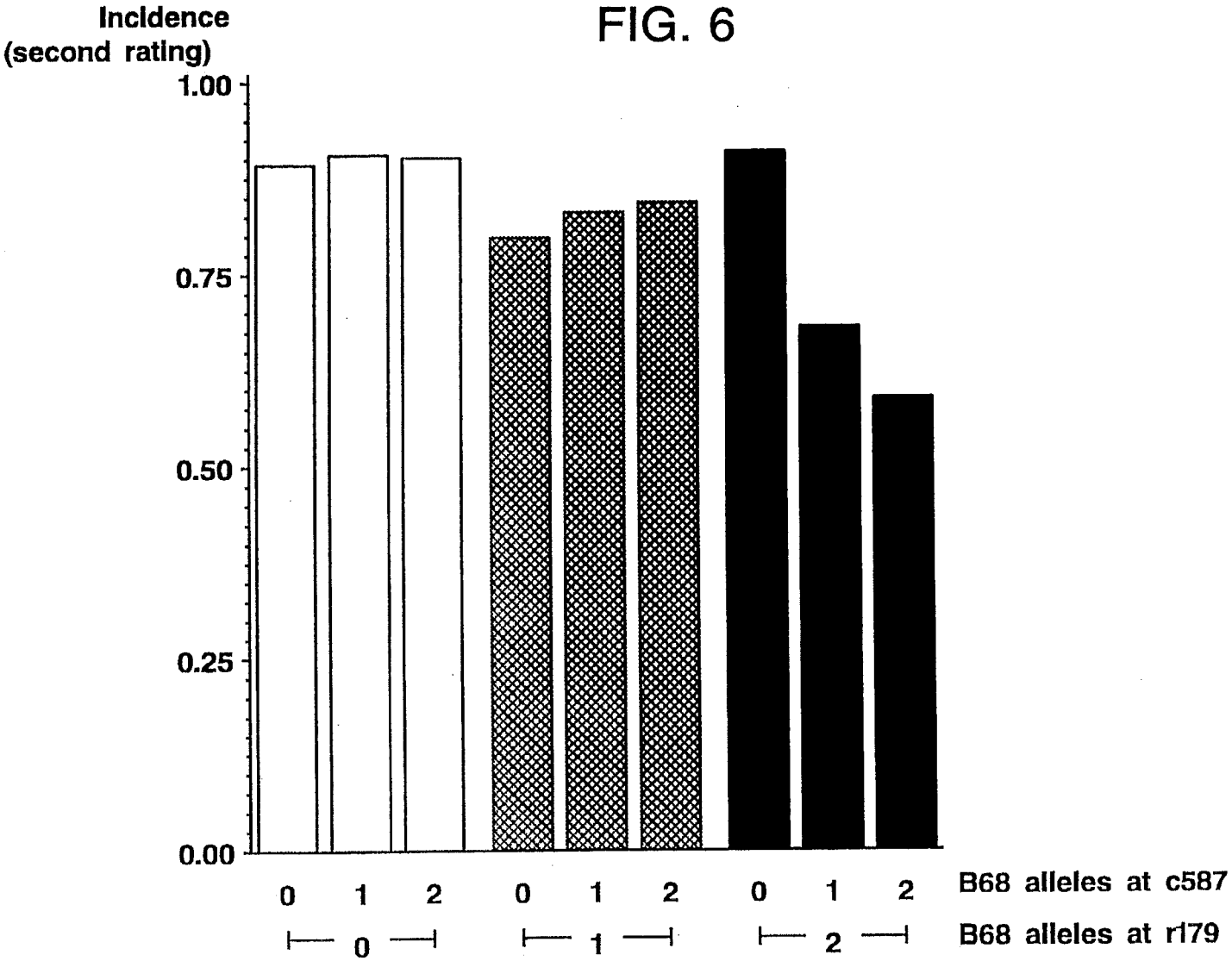
Figure 7:
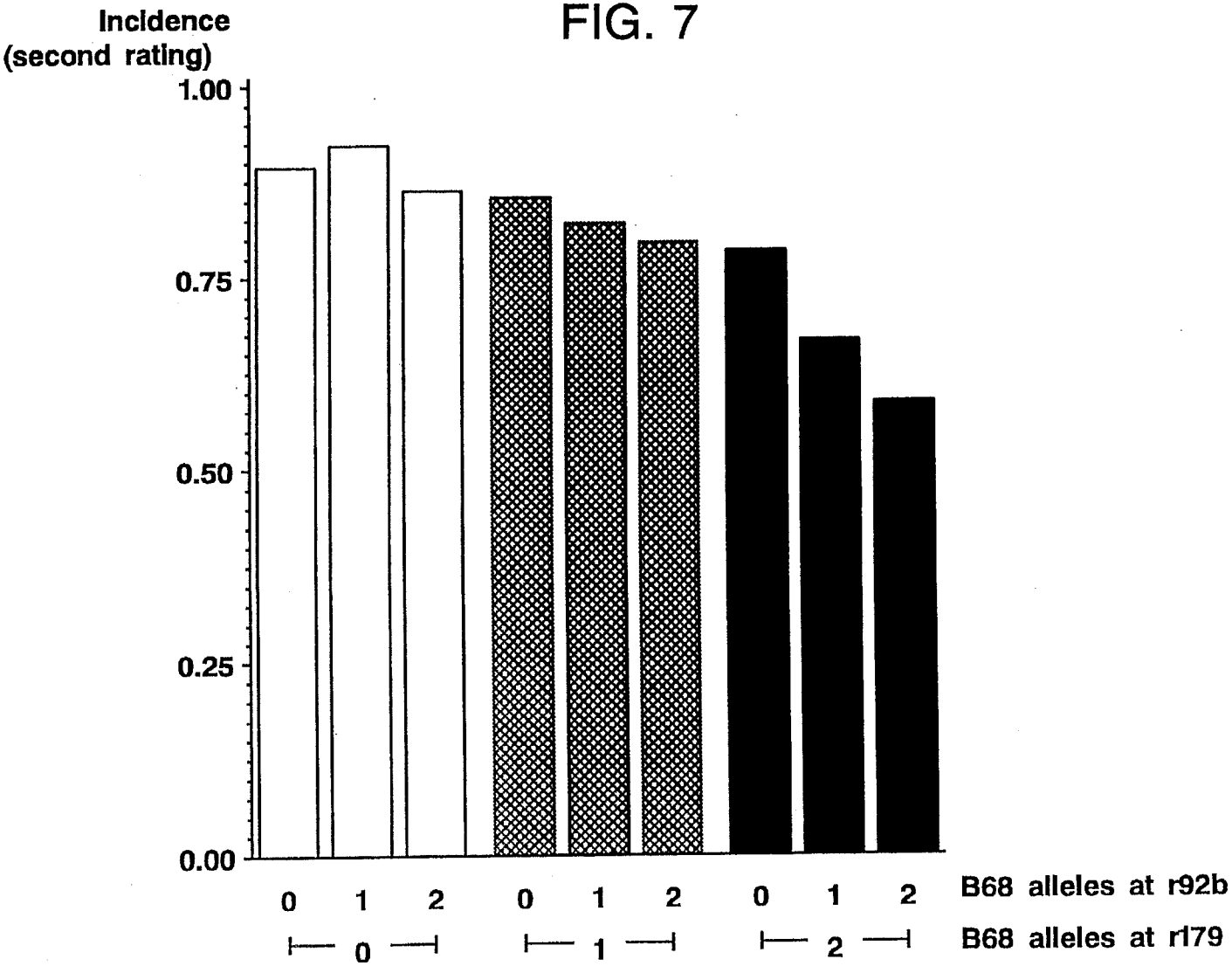

As is known to the art, DNA restriction fragment length polymorphisms (RFLP's) may be used to reveal differences in DNA taken from different organisms.

DNA is isolated from an organism and digested with a restriction enzyme by methods known in the art. A particular restriction enzyme cleaves the DNA only at sites containing a specific nucleotide sequence, e.g. the restriction enzyme EcoRI cuts double stranded DNA only in the sequences GAATTC. Each restriction enzyme will cleave the DNA of a particular organism into a particular pattern of fragments with differing lengths as specified by the distances between restriction enzyme recognition sites. Single site mutagenesis or DNA rearrangement such as insertion and deletion can alter the distance between restriction enzyme recognition sites in different genotypes. The different lengths of particular fragments distinguish genotypes and varieties. Each genotype or variety will exhibit a particular pattern or "fingerprint" of different sized fragments when probed with the same set of clones. Obviously, the more unrelated the genotypes or varieties are, the more differences there will be in their "fingerprints". Theoretically, however, even closely related inbreds could be told apart if their DNA were digested with a sufficient number of restriction enzymes and probed with a sufficient number of clones.

As is known in the art, DNA fragments may be separated by size using gel electrophoresis. When it is desired to compare the DNA of two organisms, the DNA samples of each are digested with the same restriction enzyme and the resulting fragments are separated according to size using electrophoresis. Many fragments from one genotype may differ in length from their counterparts in another genotype. Because any specific fragment represents a very small proportion of the total fragments, and cannot be distinguished from them by visual means on the gel, a sequence-specific probe which can be easily detected must be used to identify the specific homologous fragments in each DNA sample and permit comparison of fragment size.

Probes may be prepared by means known to the art, e.g. by using cDNA from RNA transcripts or genomic DNA from the organisms being studied. Plasmids containing cDNA clones used herein were made by 1) isolating poly(A) RNA from tissue, such as dark grown coleoptile tissue or root tissue from B73 maize using reverse transcriptase as is known in the art to prepare a double-stranded copy DNA (cDNA) of the RNA. Plasmids containing genomic DNA were prepared by digesting B73 inbred maize DNA to completion with the restriction enzyme XhoI or PsfI, and cloned using established methods known to the art. The bacterial plasmid vectors pSP64, pGEM3, pGEM2 and pGEMblue are examples of useful plasmids and are available from Promega Biotech, Madison, Wisconsin, and can be multiplied in suitable hosts. The specific bacterial host used above was *E. coli* MC1061.

Bacterial transformants containing the plasmids were screened using colony hybridization and DNA dot blot hybridization with radioactively labeled chloroplast, mitochondrial and nuclear maize DNA. Any colony or DNA sample which showed strong hybridization to any of the probes was rejected as containing a sequence which was organelle DNA or was highly repeated in the nuclear genome.

All of the above cloning procedures are known to the art. As is known to the art, a number of suitable plasmid vectors for the insertion of DNA sequences are available which are considered equivalent to those on deposit when bearing the clones of this invention or clones capable of hybridizing to the same genomic sequences.

Plasmid DNA isolated from each of the bacterial transformants was radioactively labeled to provide specific hybridization probes by means known to the art. In a preferred embodiment, DNA clones inserted into transcription vectors (e.g. pSP64, pGEM3 and pGEM2) may be transcribed into radioactively-labeled RNA probes using SP6 or T7 phage RNA polymerase. Alternatively, the entire plasmid or the isolated insert may be radioactively labeled by nick-translation using *E. coli* DNA Polymerase 1. All of these procedures are known in the art. These probes will hybridize to homologous sequences in any maize genome.

Markers are analyzed for their utility by hybridization to DNA prepared from inbred organisms. A donor parent is selected for exhibiting the desired phenotype, and a recipient parent is selected exhibiting other desirable phenotypes.

DNA fragments from the organisms being studied are prepared by digesting genomic DNA with a restriction enzyme. Any restriction enzyme known to the art may be used, but enzymes which meet the following criteria are preferred: 1) inexpensive, 2) reliable (i.e. not subject to manufacturer's batch to batch variation nor difficult to use ), 4 ) produce fragments ranging between about 2 and about 20 kilobase pairs, 5) exceptionally good at revealing polymorphism. Examples of preferred restriction enzymes are EcoRI, DraI, EcoRV, BclI, and BamHI. In the preferred embodiment described herein, only EcoRI was used.

After electrophoretic size separation, the DNA fragments are transferred from the electrophoresis medium (typically an agarose gel) to a solid support (e.g. nitrocellulose or nylon membranes) such that the pattern resolved on the gel is preserved on the membrane. This membrane is incubated with labelled probe during which time the probe hybridizes to the specific corresponding DNA sequence. By observing the location of the probe on the membrane, it is possible to determine differences, or "length polymorphisms", between homologous restriction fragments.

Probes which meet the following criteria are useful: 1) the probe hybridizes to a small number of genomic fragments (preferably less than three, and more preferably only one) so that the map position of each fragment can be determined unambiguously; 2) the probe must reveal polymorphism between the inbred lines that will be used to generate the segregating population used to map the clones; 3) it is desirable (though not essential) that the probe reveals polymorphism between closely related lines not necessarily pertinent to the immediate task of identifying the trait being studied; 4) the probe should produce reasonable hybridization signals and not artifactual signals which impede its routine use. The above screening procedure may be repeated using different restriction enzymes and different probes until a number of useful clones have been selected.

The above probe screening process establishes "fingerprints" or profiles of RFLP variants or alleles present in each variety. The alleles may be mapped on a chromosome map, but this is not necessary to the practice of the invention. As will be understood by those skilled in the art, markers other than RFLP probes may be part of the "fingerprint," e.g , isozyme markers and phenotypic markers and data with respect to such markers may be substituted for RFLP data in the methods described herein.

Using established methods of genetic linkage analysis, such as described in the background section of this application, the segregation data derived from the above-described crosses may be used to link genes governing the trait being studied with particular probes, and also to map the positions on the maize genome of such probes if desired. This involves calculating the percent of the progeny in which a clone cosegregates with a known marker. Genetic map distance is defined by the percent recombination observed between two loci. For example, if a given clone co-segregated with a previously mapped marker 100% of the time there would be 0% recombination and thus, the clone would be 0 cM (centiMorgans; map units) from the previously mapped marker. A 10% recombination rate would indicate a 10 cM map distance from the previous marker, etc. (Sturtevant, A. H. (1913) "The linear arrangement of six sex-linked factors in Drosophila, as shown by their mode of association", J. Exp. Zool. 14:43).

Recombination data is obtained by examining the progeny of two parental genotypes which are distinguishable by RFLP's when probed with each clone.

If it is desired to map the entire initial set of probes used to study the trait, or to determine the linkage relationships among them, linkage analysis using an improved method of orthogonal contrasts based on the method of Mather, K., "The Measurement of Linkage in Heredity" (1931) Methuen & Co., London, and the method of maximum likelihood (Allard, R. W. (1956) "Formulas & Tables to Facilitate the Calculation of Recombination Values in Heredity," Hilgardia pp. 235–278) may be used to determine recombination frequencies between the probe in question and a known marker or another previously mapped or linked probe. The Mather method is expanded to cover the 6- and 9-cell matrices required for the analysis of co-dominant traits.

If the linkage analysis indicates that an association of a clone with another marker exists, a test of maximum likelihood is performed, as known to the art, to estimate the recombination frequency (also called "linkage" or "association") of the two traits or probes. This recombination frequency is designated p by convention. The standard error of this recombination frequency is also calculated by methods known to the art. The value of p is an estimate and because the recombination frequency can be thought of in terms of map units of separation, it indicates the most likely distance between two markers. The standard error is symmetrically distributed about the value p and indicates the range within which the true distance between markers is expected to lie. The stringency of the linkage analysis is such that p values will rarely exceed 0.20 (20 map units).

The process is repeated with all selected probes. The association of each marker used in a particular cross is compared with each other marker which can be used to differentiate the parents used in that cross. In this way one cross generating between preferably about 50 to about 100 F2 individuals can be used to analyze a large number of markers.

Associated markers are arranged in linear order to form "linkage groups".

Linkage groups may be assigned to any of the chromosomes of the organism based on associations of markers in the group to markers previously mapped to these chromosomes, or by the use of other means known to the art such as analysis of monosomics. This latter method is well known to the art and is described, e.g., in T. Helentjaris et al. (1986) "Use of Monosomics to Map Cloned DNA Fragments in Maize", supra, incorporated herein by reference.

Recombination frequencies are not strictly analogous to physical distances since factors other than absolute separation on the chromosome may determine recombination rates. For this reason, map distances assigned to each marker are approximations of least inconsistency and represent therefore a compromise whereby map distances simply approximate recombination frequencies as closely as possible.

As an alternative to the development of a special set of probes covering the genome of the organism, such probes previously developed by the prior art may be used. Probes useful for studying traits in maize and their map locations are known to the art, as described in the background section.

It is useful but not necessary to determine the linkage relationships between the initial set of probes used to determine polymorphisms between the parent organisms prior to analyzing them for the contribution to a particular polygenic trait.

It is preferred that the probes used have only one locus in the genome, however, if probes having more than one locus must be used, they can be identified by band size which, as known to the art, may be ascertained by determining the band size linked to a probe also having an effect on the expression of the trait.

In the preferred embodiment, a trait, preferably one suspected to be polygenically determined, is selected for study. Parental organisms, preferably inbred lines, exhibiting the trait and not exhibiting the trait are chosen, and preferably the parent or inbred not exhibiting the trait is selected for otherwise desirable genomic material. This parent is called the "elite" parent. DNA from the parents are probed with the initial set of probes to determine which probes show polymorphisms when the parental DNA is compared.

Progeny segregating for the trait are selected, and preferably backcrossed to the elite parental line to maximize elite DNA, and selfed to produce individuals homozygous for the trait in question.

Progeny from the parental cross are analyzed using the initial set of markers to determine marker genotypes, or "fingerprints."

The progeny population resulting from the above-described crosses, and preferable backcrosses and selfing, is analyzed using the markers showing polymorphisms between the parents, and in addition is rated for the presence of the trait being studied. The percent of individuals exhibiting the trait in the population is termed the "incidence" herein. When the trait is one which can be rated quantitatively, such as for severity or intensity, as is MDMV resistance/susceptibility, it is preferred that this parameter be rated as well. This parameter is termed "severity" herein. Preferably, severity is rated on a scale yielding no more than about three or four values, such as the scale of 1 to 4 used in the preferred embodiment hereof. It is also preferred that several ratings, preferably about three, be taken over the life cycles of the individuals being rated so as to ensure that the presence of the phenotype is detected. Preferably incidence times severity are considered together in a single factor for evaluation, and the separate ratings during the life cycles of the individuals are separately evaluated.

As is known to the art, the effects of factors other than genotype on the ratings may be accounted for by appropriate experimental designs as is known to the art.

Preferably, the data with respect to RFLP probe alleles and observation of the trait being studied is analyzed by multiple regression by leaps and bounds ("leaps"), as described in Furnival, G. M. and Wilson, Jr., R. W. (1974),l "Regression by leaps and bounds," Technometrics 16:499–511, to determine a subset of probes accounting for a maximum amount of phenotypic variation, followed by multiple standard regression as is known to the art to determine the relative contribution of each probe to the phenotype.

Multiple regression by leaps and bounds requires a high degree of computer capacity, and the method may need to be adapted, as discussed in the Examples hereof, to the available computer capacity. It is assumed that the presence of each donor allele in the DNA at a given locus contributes an equal amount to the presence of the phenotype.

The "leaps" analysis results in a manageable number of loci and associated primary probes, which account for the maximum presence of the trait, and are therefore said to be linked to the trait. By examining the successive sets of marker loci chosen by "leaps," flanking probes may be identified which are associated with the trait at each locus, but not as closely as the primary probes.

The multiple regression is performed on the smaller set of primary probes identified by "leaps." This analysis shows the relative contribution of each marker locus to the total explained phenotypic variance, compares the degree of explained variance across different times of rating, and generates data ("residuals") whose magnitude and distribution may be used to determine epistasis.

When a normal quantile quantile plot of residuals shows deviation from the expected straight line, rising steeply at the high end, and lowering steeply at the low end, indicating that the trait is markedly more pronounced than a simple additive effect for each marker locus allele would indicate when maximal presence of the trait is predicted by the presence of appropriate marker alleles, and markedly less pronounced than expected when the relative absence of the trait is predicted by the presence of appropriate marker alleles, epistasis is suspected. Examination of the effects of the presence or absence of particular alleles at particular loci when alleles at one or more additional loci are present or absent, for example as shown in the Figures, shows which loci and combinations of loci ar most effective in accounting for the trait. Probes at these marker loci may then be preferentially selected for use in manipulation of the trait in progeny populations.

RFLP analysis of progeny selected by backcrossing and selfing for homozygosity of the desired trait along with maximum presence of the elite genotype will identify those individuals with DNA governing the trait but a minimum of surrounding donor DNA. Individuals who are heterozygous or homozygous for recipient parent alleles at flanking marker loci, preferably those which are homozygous for recipient parent alleles at such flanking sites, are selected for further breeding. Without the use of the RFLP technology described herein, it would be virtually impossible to identify rare individuals having the trait but minimal surrounding donor DNA when donor DNA tends to move in clumps, as does the B68 DNA used in the examples hereof.

The following Examples are provided by way of illustration and not in limitation of this invention. As will be apparent to those skilled in the art, alternative means exist for accomplishing many of the steps described in the examples and may be substituted therefor.

EXAMPLES

Example 1

Genetic Stocks and Breeding Scheme

The inbreds B68HtHt and B73 HtHtrhmrhm, originally released by Iowa State University, Ames, Iowa, were used in this experiment. The gene designations Ht and rhm indicate that the accessions used are resistant to Helmithosporium turicum race I, and Drechslera maydis, race (formerly Helmithosporium maydis). B68HtHt, a known source of Maize Dwarf Mosaic Virus resistance (Mikel, M. A. et al. (1984), "Genetics of resistance of two dent corn inbreds to maize dwarf mosaic virus and transfer of resistance into sweet corn," Phytopathology 74(4):467), was used as the female in the initial cross with B73, an MDMV susceptible line. The F1 was then selfed to produce F2 seeds and 157 F2 plants were selfed in the greenhouse resulting in 109 F3 progeny lines.

F3 Progeny lines were tested for MDMV resistance at two locations (Farmington, Minn. and Madison, Wis.) using two blocks per location in a randomized complete block design. The parental lines, a susceptible sweet corn hybrid (Jubilee), and a resistant dent corn hybrid (8100, Jacques seed) were included in each block.

Remnant seed from the most resistant F3 progeny line was then backcrossed to B73HtHtrhmnrhm female. The seed from three backcross plants was bulked, planted out and selfed at Madison. Four seeds from each S1 ear were bulked and selfed again. 120 intact S2 ears were selected at random from approximately 300 ears obtained. The S2 seed was tested for MDMV resistance at Lincoln, Ill. and Madison Wis. using a balanced incomplete block design with 34 entries per incomplete block, and four replications of each incomplete block. Each incomplete block included 30 progeny lines, a resistant dent corn check (LH151), the susceptible check Jubilee, and the original parental lines.

Example 2

Molecular methods 2.1 DNA extraction:

Second ear husk tissue, harvested at the silking stage, was used to isolate F2 DNA samples. For S2 progeny, leaf tissue samples from 12 field-grown plants at the 3–5 leaf stage were pooled and the DNA extracted.

Crude nuclei were nuclei by a modification of Murray, M. G. and Kennard, W. C. (1984), "Altered chromatin conformation of the higher plant gene phaseolin," Biochemistry 23:4225. Nuclei extraction buffer contained 20 mM Pipes (pH7), 3 mM$MgCl_2$, 0.5M hexylene glycol, 10 mM orthophehanthroline, 10 mM sodium metabisulfite and 200 μM aurintricarboxylic acid. Crude nuclear pellets (500×g, 10 min.) were lysed in 15 mM EDTA, 0.7M NaCl, 0.5% cetyltrimethyl ammonium bromide and 10 μg/ml proteinase K for 1 hour at 65° C. Insoluble material was removed by centrifugation (10,000×g 10 min.) and the DNA precipitated by addition of ammonium acetate and isopropanol to final concentrations of 1.25M and 50% respectively. DNA was dissolved in DNA dialysis buffer containing 2 μg/ml RNAse A and incubated several hours at 37° C. After phenol extraction, the DNA was reprecipitated with isopropanol, rinsed and dissolved in DNA dialysis buffer. DNA concentrations were determined fluorometrically (Murray, M. G. and Paaren, H. E. (1986), "Nucleic acid quantitation by continuous flow fluorimetry," Anal. Biochem. 154:638–642.

2.2 Electrophoresis and Blotting:

Five μg of restricted DNA was typically loaded into 2.7 mm wide lanes cast in 0.75% agarose gels made in 100 mM Tris-acetate (pH 8.3), and 2.5 mM EDTA. Electrophoresis was at 1 volts/cm for 15–18 hours. Gels were stained for 30 min. in 0.1 μm/ml ethidium bromide prior to photography and UV nicking. A short wave UV dose of 1400 $\mu W/cm^2$ (one min. from one 15 watt germicidal bulb at a distance of 6 cm) was sufficient to introduce 1 nick per 3–4 kb and optimize transfer from the gel. We found UV nicking to be faster and more easily controlled than acid depurination. The gel was denatured in 150 mM NaOH and 3 mM EDTA for 20 minutes, rinsed briefly in distilled water and neutralized for 20 minutes in 150 mM sodium phosphate buffer (pH 7.8). Gels were transferred onto Genetran 45 or Zetabind membranes by capillary blotting using 10 mM sodium pyrophosphate (pH 9.8 ) as the transfer buffer. The membranes were soaked for at least 10 minutes in sodium pyrophosphate prior to transfer and dried thoroughly following transfer. Membranes were blocked for 2 to 3 hours at room temperature in 2% SDS, 0.5% BSA and 1 mM EDTA prior to their first use.

2.3 Probe Preparation and Hybridization:

RNA marker loci prepared with the Riboprobe (Promega, Madison Wis.) system to a specific activity of about 8 to $1.2\times 10^8$ cpm/μg were used throughout this study. Plasmids were prepared according to Kieser, T. (1984), "Factors affecting the isolation of CCC DNA from *Streptomyces lividans* and *Escherichia coli*," Plasmid 12:19–36, and linearized to prevent transcription into the vector.

Blots were prehybridized overnight at room temperature in 100 mM sodium phosphate buffer (pH 7.8), 20 mM sodium pyrophosphate, 5 mM EDTA, 1 mM orthophenathrolinhe, 0.1% SDS, 500 μg/ml heparin sulfate 10% dextran sulfate, 5 μg/ml poly(C), 50 μg/ml herring Sperm DNA. Probe was added to a final concentration of 2–500,000 cpm/ml. It was frequently possible to mix 3 marker loci at a time once the migration of each band was known. After 6 hours at 65° C. blots were rinsed in excess wash buffer (20 mM NaPB (pH 8.6), 5 mM NaPPi, 1 mM EDTA and 0.1% SDS) for 30 minutes at 65° C. Blots were incubated in RNAse solution (50 ng/ml RNAse A in 300 mM NaCl, 5 mM EDTA and 10 mM Tris-HCl (pH 7.5)) for 15 minutes at room temperature followed by the addition of proteinase K and SDS to 10 μg/ml and 0.1% respectively and incubation for 15 minutes at room temperature. Blots were given two final 15 minute washes in half strength wash buffer at 65° C. Blots were autoradiographed on Kodak XAR 5 film using one DuPont Cronex Lightning Plus intensifying screen at −80° C.

Example 3

Virus inoculation

Stocks of MDMV-A or MDMV-B were obtained from Jacques Seed Co., Prescott, Wis. in the form of infected sorghum plants. Stocks were subsequently verified by their ability to grow on sudan grass or Johnson grass (Compendium of Corn Diseases, 2nd Edition (1980) (Shurtieff, M. C. ed.), 61– 63). To prepare sufficient inoculum for field experiments, 100 g of sorghum leaf tissue was homogenized in 600 mls ice cold 0.1M potassium phosphate buffer (pH 7.4) using a Cuisinart food processor. Debris was removed by filtration through cheesecloth and 0.01 g/ml of corrundum (#22 Mm) was added prior to immediate application with sprayer at 60 psi. Virus was amplified on the Jubilee variety of sweet corn (source: Rogers Bros. Seed Company), a line especially sensitive to MDMV. Twenty-five four-leaf stage plants were inoculated with MDMV-A and 25 with MDMV-B in the greenhouse. Inoculation was repeated two days later. After six weeks, large quantities of field inoculum were prepared as above from equal weights of MDMV-A and MDMV-B infected Jubilee tissue.

F3 progeny lines were inoculated twice, five days apart, at the 3–5 leaf stage with the mixed MDMV-A and MDMV-B inoculum. Plants were scored for incidence and severity 2, 4 and 6 weeks later. Incidence was calculated as number of plants infected over number of plants in the row. The criterion for presence of virus was the characteristic mosaic symptom on any leaves, regardless of extent. Every leaf on each plant was inspected, except for the last rating, in which leaves at eye level or below were examined. Severity was rated on scale of 1–4 where 1 was an isolated streak of mosaic following the venation (1 streak/leaf on not more than two leaves), and 4 was a severely chlorotic, dwarfed plant with mosaic present on all visible leaves. A rating of two or more indicated systemic disease.

Because of the scale of the S2 field experiment and the need to ensure adequate and consistent infectivity, inoculum was prepared on site (i.e. in the field) from potted infected plants. S2 plants were inoculated once at the 3–5 leaf stage. Inoculation at the Madison site was done three days after tissue was taken for DNA extraction. S2 plants were rated 2, 4, 6 and 8 weeks after inoculation for both incidence and severity. Given ratings were completed in one day, and each rating was begun at different starting points to minimize the effect of human fatigue.

Example 4

Statistical analysis

Statistical analysis used UNIX and S software installed on a Pyramid model 90X computer (Mountain View, Calif.). Fifteen F3 genotypes were either lost or discarded due to poor stand (<50% of seeds planted), loss of F2 DNA sample, or insufficient F2 DNA. The statistical analysis described below included the 93 genotypes retained in the initial experiment.

Both field experiments were analyzed as two levels factorials (genotype and location) with repeated measures (time), after block or incomplete block effects were accounted for. Incidence data was transformed using arsin of sqrt of p to stabilize the variance.

The assessment of genetic linkage was done using the classical method of phenotypic categories as described by Mather, K. (1931), "The measurement of linkage in heredity," Methuen & Co., London, with additional orthoganal coefficients added to account for the 9-cell classification expected for the comparison of two codominant markers. The method of maximum likelihood (Allard, R. W. (1956), "Formula E Tables to Facilitate the Calculation of Recombination Values in Heredity," Hilgardia 235–278, was used to calculate linkage.

The phenotypic data (Y data) used were the disease scores for incidence and incidence x severity for each rating done at 2, 4 and 6 weeks after inoculation. The incidence and incidence x severity data within a given rating were considered to be separate factors, while each rating in time was kept separate, thus yielding a total of six sets of Y values. As the desirable trait would yield a number close to zero, all loci homozygous for the B68 morphs were coded to the number zero, while the loci homozygous for the B73 morphs were coded to the number 2, and heterozygotes were then coded as 1. Marker loci which yielded five or more missing values were dropped (5 of 76). For those marker loci yielding 4 or fewer missing values, the value of any missing data was estimated by using the value of the marker locus most closely linked to the marker locus with missing data for the individual in question. There were a total of 44 estimated missing values in a data set composed of 6603 values (93 F3 individuals and 71 marker loci).

The potential association between the dependent variable Y (the F3 disease rating) and the independent variable X (the set of morphs for a given marker locus) was initially assessed using Mallows' method of multiple regression by leaps and bounds (Furnival, G. M. and Wilson, Jr., R. W. (1974), "Regressions by leaps and bounds," Technometrics 16(4):499–511) in which the criteria for subset selection is based on the test statistic Cp. The calculation of Cp results in a trade-off between maximizing the predictive value of the model while minimizing the number of variables in the selected subset (Weisberg, S. (1985), "Applied Linear Regression," (2nd edition)). The calculations which generate the subset values utilize two algorithms from a larger set which if used together compute the residual sums of squares for all possible regressions. These two algorithms can be combined to form a leap operation for finding the best subsets without examining all possible subsets.

After leaps and bounds was done on each set of Y data, the marker loci selected were reanalyzed using the standard multiple regression. The multiple regression analysis was used to compare the relative contribution of each marker locus to the total explained phenotypic variance, to compare the degree of explained variance (the multiple $R^2$ value) across different times of rating, and to examine the magnitude and distribution of residuals.

The phenotypic scores of S2 population were handled in the same way as described above. The phenotypes of the S2 population were assessed by multiple regression using the set of marker loci selected, for all four disease ratings for incidence and incidence x severity.

Comparisons of the expected versus observed genotypes in the F2 were done using the Chi-square goodness of fit statistic. Calculation of allele frequency in the S2 was done using the Hardy-Wineberg expectation ($p^2+2pq+q^2$) where $p^2$ was the observed frequency of B68 homozygotes at a given locus, and $q^2$ the observed frequency of B73 homozygotes.

Example 5

Field data

The anova for the field data revealed no significant differences between blocks at locations or between locations, for either incidence (I) data or incidence x severity (S) data. The differences between the times of rating, however, were highly significant ($p<0.001$ I and S data). Examination of mean scores by genotype for each rating revealed a general tendency for incidence and severity to increase slightly with time. However, eight F3 progeny lines showed a decrease in incidence between the first and last ratings of 15% of more, while in 12 lines incidence increased by 15% or more. The most dramatic drop occurred in line 117, in which the initial incidence of 0.24 dropped to 0.04. With the exception of 117, the severity ratings for those lines in which incidence decreased indicated that some plants in the row developed systemic infection, while others appeared to "outgrow" or contain the virus. The donor parent B68, line 117, and line 141 were the only entries in which no plants developed systemic disease. Line 141 was chosen as the donor for the backcross to B73 on the basis of consistently low incidence (0.09, 0.14, 0.09) and severity (1.2, 1.0, 1.4) ratings. At the time of this choice, the genotype of the F2 plant "141" which produced this line was unknown. We made the assumption that F2 plant "141" must have been homozygous for the majority if not all of the resistance genes from B68 in order to have produced a line which was at least as resistant as B68 itself in the year in which the ratings were done.

Example 6

Prediction

We chose to use a linear regression approach to identifying marker loci linked to genes contributing to MDMV resistance. The restriction fragment length polymorphisms were considered the independent variable (X data). The genotype homozygous for the B68 morphs at a given marker locus was scored as "0," the heterozygous genotype as "1" and the genotype homozygous for the B73 morphs as a "2." This method of weighting genotypes assumes that each B73 allele at each locus gives one "hit" of susceptibility, and assumes no interactions between different loci. The effect of potential recombination was not considered other than in the implicit sense that the observed phenotypic variability would be best accounted for by those loci which were most tightly linked to resistance genes. Our computing capacity was such that 71 probes could not be evaluated simultaneously. We constructed a computer program which performed linear regression by leaps and bounds using 20 probes at once. To reduce potential bias due to the order in which the groups of marker loci were analyzed, the program made recursive assessments of the data, beginning with the first 20 probes, proceeding to probes 5–25, 10–30, 15–35, etc, until the remaining number of probes was less than 15. These last probes were then combined with the first five in the set, and the final recursive regression done. The order of the 71 probes was then randomized and the analysis was repeated. Each time leaps was performed, the program saved the best ten probe combinations. All of the marker loci subsets selected by leaps were again presented to leaps, and assessed recursively as before. The subset selections from this analysis were then combined and run again until a single subset remained. This entire process was done on each of three sets of marker loci data. Each set contained the same data, but the order of the data was randomized within each set. The dependent variable Y consisted of six separate data sets; the three time ratings for the I data and the three time ratings for the S data. Regression by leaps and bounds was performed as described above for each set of Y data.

Upon completion of the analyses, the nine sets of marker loci for the I data (three time ratings for each of three randomized sets of X data) and the nine sets of marker loci for the S data were compared. Those marker loci which were chosen in all three data sets for each time rating for I data and S data were compared (Table 1). From this comparison the marker loci r179, gp144, c262, c512, c329, r271, r250, r189, c92b, c926, r324 and r248a were chosen for further investigation.

The first set of markers tested did not include markers r271, r189, r250, r324, and r248a (Table 2). The marker loci chosen accounted for 93–95% of the observed phenotypic variance for incidence, and 91–93% of the observed phenotypic variance for incidence times severity. A test of the relative contribution of r250 versus c512 was

TABLE I

Markers chosen by "Leaps"
Three random data sets for each disease rating

One set of Incidence (INC) data composed of three ratings, each of which has three subsets of markers chosen by leaps using the same group of marker loci, but analyzed in different orders to attenuate bias due to the order in which markers are evaluated. Similarly for the Incidence X Severity (INC X SEV) data.
Markers chosen only once in each set of three per each rating are deleted.
Markers chosen only within a single rating are deleted.
Markers chosen only within INC set or INC X SEV set are shown if above criteria are met.

| | | | |
|---|---|---|---|
| INC 1 | | | |
| r179 gp144 c512 | | c329 r262 | r271 |
| r179 gp144 c512 | | c329 r262 r92b* | r271 r189 r250 r324 |
| r179 gp144 c512 | | c329r92b | r271 r189 r250 r324 |
| INC 2 | | | |
| r179 gp144 c512 | | c329 r262 r92b | r271 |
| r179 gp144 c512 | | c329 r262 r92b | r271 r189 r250 |
| r179 gp144 | | c329 r262 | r189 r250 |
| INC 3 | | | |
| r179 gp144 c512 | c926 | r262 r92b | r271r250 |
| r179 gp144 c512 | c926 | c329 r262 r92b | r271 r189 r250 r324 |
| r179 gp144 c512 | | c329r92b | r189r324 |
| INC X SEV 1 | | | |
| gp144 | | r262 | r189 r250 |
| gp144 | c587 c926 | r262 | r189 r250 |
| gp144 | c587 c926 | r262 | r189 r250 |
| INC X SEV 2 | | | |
| r179 gp144 | c587 | r262 r92b | r271r250 r248a* |
| r179 gp144 | c587 | r262 r92b | r271r250 r248a |
| r179 gp144 | c587 | r262 r92b | r271r250 r248a |
| INC X SEV 3 | | | |
| r179 gp144 c512 | c587 c926 | r92b | r248a |
| r179 gp144 | c587 | c329r92b | r189r248a |
| r179 gp144 c512 | c587 c926 | c329r92b | r189 |

Inspection of previously determined linkage data reveals that of the markers selected above, the following are linked pairs: r179–r271, gp144–r189, c587–c512–r250.
*a and b designations indicate the probe was found to map to more than one locus on the genome.

TABLE 2

Multiple Regression Analysis of Eight Probes
Most Consistently Chosen by Leaps and Bounds
Across Times of Rating
(Flanking Markers not Included)

| | Coef | Std Err | t Value |
|---|---|---|---|
| Regression on first rating for Incidence | | | |
| r179 | 0.1920859 | 0.03979275 | 4.827157 |
| gp144 | 0.2035315 | 0.04309700 | 4.722638 |
| c926 | 0.0841703 | 0.04116961 | 2.044477 |
| c329 | 0.1418603 | 0.04016558 | 3.531886 |
| c587 | 0.0739064 | 0.05554563 | 1.330554 |
| c512 | 0.0933097 | 0.05278113 | 1.767861 |
| r262 | 0.1148176 | 0.04179766 | 2.746986 |
| r92b | 0.1150422 | 0.03853215 | 2.985616 |
| Residual Standard Error = 0.2660565 | | | |
| Multiple R Square = 0.949127 | | | |
| N = 95 F Value = 202.8943 on 8, 87 df | | | |
| Regression on second rating for Incidence | | | |
| r179 | 0.1795560 | 0.04350730 | 4.127032 |
| gp144 | 0.2010054 | 0.04712000 | 4.265820 |
| c926 | 0.0948380 | 0.04501268 | 2.106917 |
| c329 | 0.1550757 | 0.04391493 | 3.531274 |
| c587 | 0.0639720 | 0.06073067 | 1.053371 |
| c512 | 0.1139893 | 0.05770811 | 1.975274 |
| r262 | 0.1092032 | 0.04569936 | 2.389599 |
| r92b | 0.1428178 | 0.04212903 | 3.390010 |
| Residual Standard Error = 0.2908921 | | | |
| Multiple R Square = 0.944296 | | | |
| N = 95 F Value — 184.3544 on 8, 87 df | | | |
| Regression on third rating for Incidence | | | |
| r179 | 0.1661475 | 0.04313687 | 3.851635 |
| gp144 | 0.1767770 | 0.04671880 | 3.783851 |
| c926 | 0.1046542 | 0.04462944 | 2.344960 |
| c329 | 0.1427865 | 0.04354103 | 3.279355 |
| c587 | 0.0925554 | 0.06021359 | 1.537118 |
| c512 | 0.0967427 | 0.05721676 | 1.690810 |
| r262 | 0.0876406 | 0.04531026 | 1.934232 |
| r92b | 0.1584079 | 0.04177032 | 3.792355 |
| Residual Standard Error = 0.2884154 | | | |

TABLE 2-continued

| Multiple Regression Analysis of Eight Probes Most Consistently Chosen by Leaps and Bounds Across Times of Rating (Flanking Markers not Included) | | | |
|---|---|---|---|
| | Coef | Std Err | t Value |
| Multiple R-Square = 0.941025 | | | |
| N = 95 F Value = 173.5252 on 8, 87 df | | | |
| Regression on first rating for Incidence × Severity | | | |
| r179 | 0.4811642 | 0.1010414 | 4.762049 |
| gp144 | 0.4055680 | 0.1094315 | 3.706134 |
| c926 | 0.2045853 | 0.1045375 | 1.957051 |
| c329 | 0.2108138 | 0.1019881 | 2.067043 |
| c587 | 0.2204143 | 0.1410410 | 1.562768 |
| c512 | 0.1583903 | 0.1340214 | 1.181829 |
| r262 | 0.1601508 | 0.1061323 | 1.508974 |
| r92b | 0.1410394 | 0.0978405 | 1.441523 |
| Residual Standard Error = 0.675568 | | | |
| Multiple R-Square = 0.915254 | | | |
| N = 95 F Value = 117.4491 on 8, 87 df | | | |
| Regression on second rating for Incidence × Severity | | | |
| r179 | 0.4449658 | 0.1035316 | 4.297872 |
| gp144 | 0.3822563 | 0.1121286 | 3.409090 |
| c926 | 0.2311180 | 0.1071139 | 2.157684 |
| c329 | 0.2125058 | 0.1045017 | 2.033516 |
| c587 | 0.3336661 | 0.1445170 | 2.308835 |
| c512 | 0.1345009 | 0.1373244 | 0.979439 |
| r262 | 0.1642594 | 0.1087479 | 1.510460 |
| r92b | 0.1652890 | 0.1002518 | 2.646226 |
| Residual Standard Error = 0.6922181 | | | |
| Multiple R-Square = 0.923701 | | | |
| N = 95 F Value = 131.6558 on 8, 87 df | | | |
| Regression on third rating for Incidence × Severity | | | |
| r179 | 0.5146590 | 0.1072424 | 4.799024 |
| gp144 | 0.3747488 | 0.1161475 | 3.226491 |
| c926 | 0.2349898 | 0.1109531 | 2.117920 |
| c329 | 0.2335804 | 0.1082472 | 2.157841 |
| c587 | 0.2487058 | 0.1496968 | 1.661396 |
| c512 | 0.1687855 | 0.1422464 | 1.186571 |
| r262 | 0.0577514 | 0.1126457 | 0.5126821 |
| r92b | 0.3200847 | 0.1038451 | 3.082320 |
| Residual Standard Error = 0.717029 | | | |
| Multiple R-Square = 0.918324 | | | |
| N = 95 F Value = 122.2729 on 8, 87 df | | | |

done by substituting the former for the latter and repeating the multiple regression. Although the multiple $R^2$ values were not significantly different (0.9446, r250 vs. 0.9443, c512), the partial regression coefficients of c512 were consistently, although slightly higher. From this results we concluded that the gene of interest probably lay between c512 and r250. A similar approach was used for the r179–r271 pair and the gp144–r189 pair. As r206, the closest marker to r179 on side opposite to that of r271, was not included in the final assessment by leaps and bounds, we concluded that the gene of interest was between r179 and r271, and closer to r179. Although no marker was available for gp144 on the side opposite to that of r189, the magnitude of the partial regression coefficients associated with gp144 and r189 indicated that these loci marked the segment in which the gene of interest was located. The relative contributions of r324 and r248a were assessed by adding each, one at a time, to the list shown in Table 2. The multiple $R^2$ values were not significantly increased, and the partial regression coefficients indicated minimal positive effects. As the purpose of the experiment was to predict resistance in a progeny population using the minimum number of markers for the best possible prediction, these two markers were not included in the set which was used for prediction of phenotype in the S2 progeny.

The coefficients of partial regression revealed that the relative importance of each marker locus changed somewhat across different rating times. The partial regression coefficients express the average change in standard deviation units of the Y data for one standard deviation unit of marker locus under consideration when the effect of all the other loci are kept constant (Sokal, R. R. and Rohlf, F. J. (1981) Biometry (2nd edition). The partial regression coefficient of r179 for the first rating of the S data for example, is interpreted to mean that for those genotypes having the same score for each of the other loci (all zeros, or all ones or all twos), an increase of one standard deviation in the value of r179 (an increase towards B73 morphs and away from B68 morphs) results in an increase of the S data score by 15% of its standard deviation. The total effects of all the partial regression coefficients are not necessarily additive because the X values or the marker loci values are correlated with each other. The magnitude of interdependence case may be calculated by dividing the standard error shown by the standardized unexplained variance $(1-R^2)/(n-k-1)$, where $R^2$ is the multiple $R^2$ value, n is the population size, and k is the number of variables. The number thus obtained (i.e. 0.0435/((1–0.9443)/86)) = 67.16 for r179, second incidence rating), is the variance inflation factor (Marquardt, D. W. (1970), "Generalized inverses, ridge regression, biased linear estimation, and nonlinear estimation," Technometrics 12:591–612), and represents the factor by which the unexplained variance is inflated due to intercorrelation among the independent variables. The variance inflation factor will equal unity if the X variables are uncorrelated. Although the VIFs do not indicate how the intercorrelation obtains, the evidence of lack of independence between the variables in an additive genetic model suggests a degree of epistatic interaction. Normal quantile quantile plots of residuals showed excellent fit to a linear model within the moderately resistant to the moderately susceptible genotypes, but significant departure from linearity was observed for both the most resistant and the most susceptible genotypes. The pattern of these deviations also suggested an interaction between one or more of the marker loci.

Figure 8:
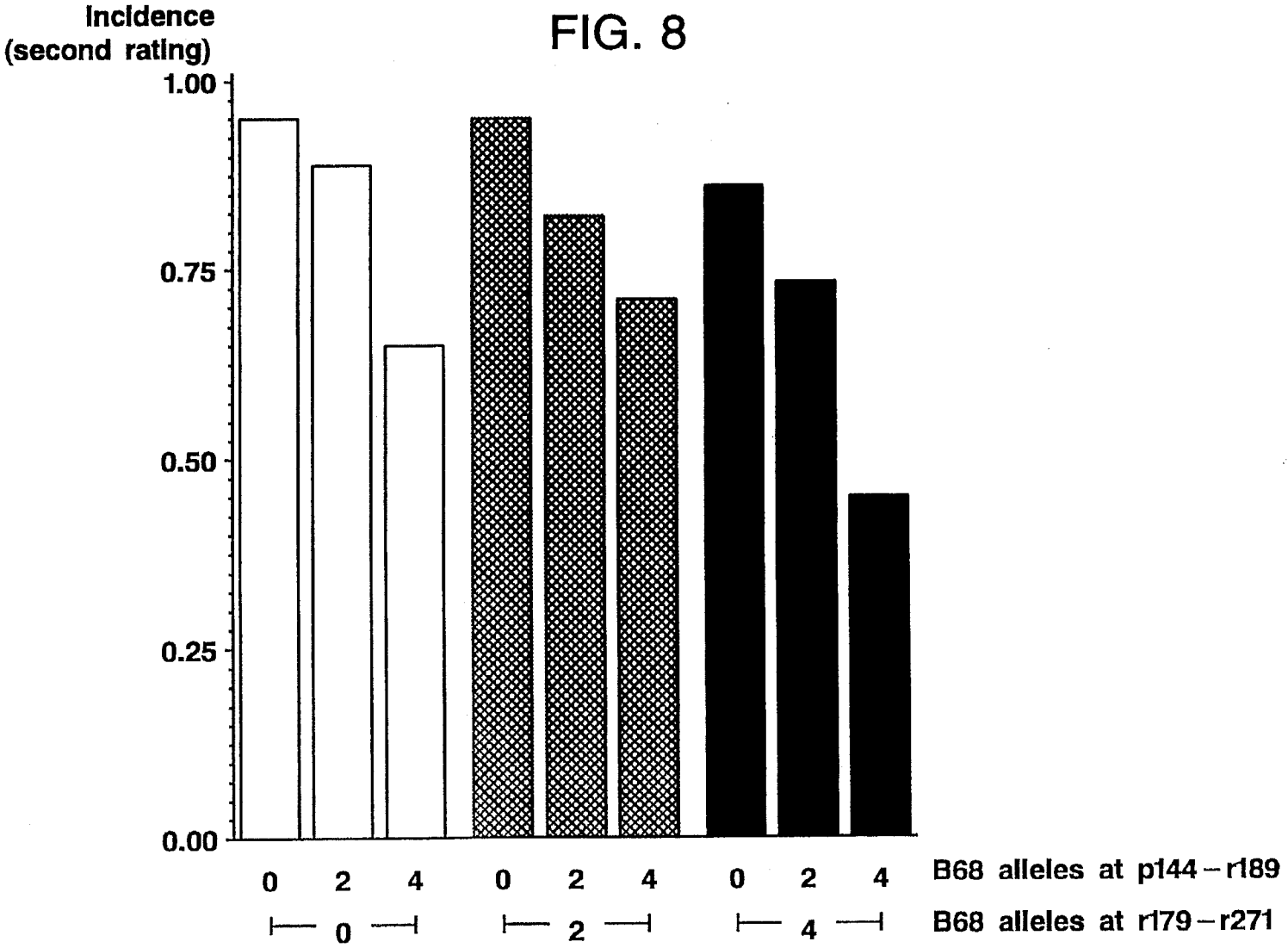
Figure 9:
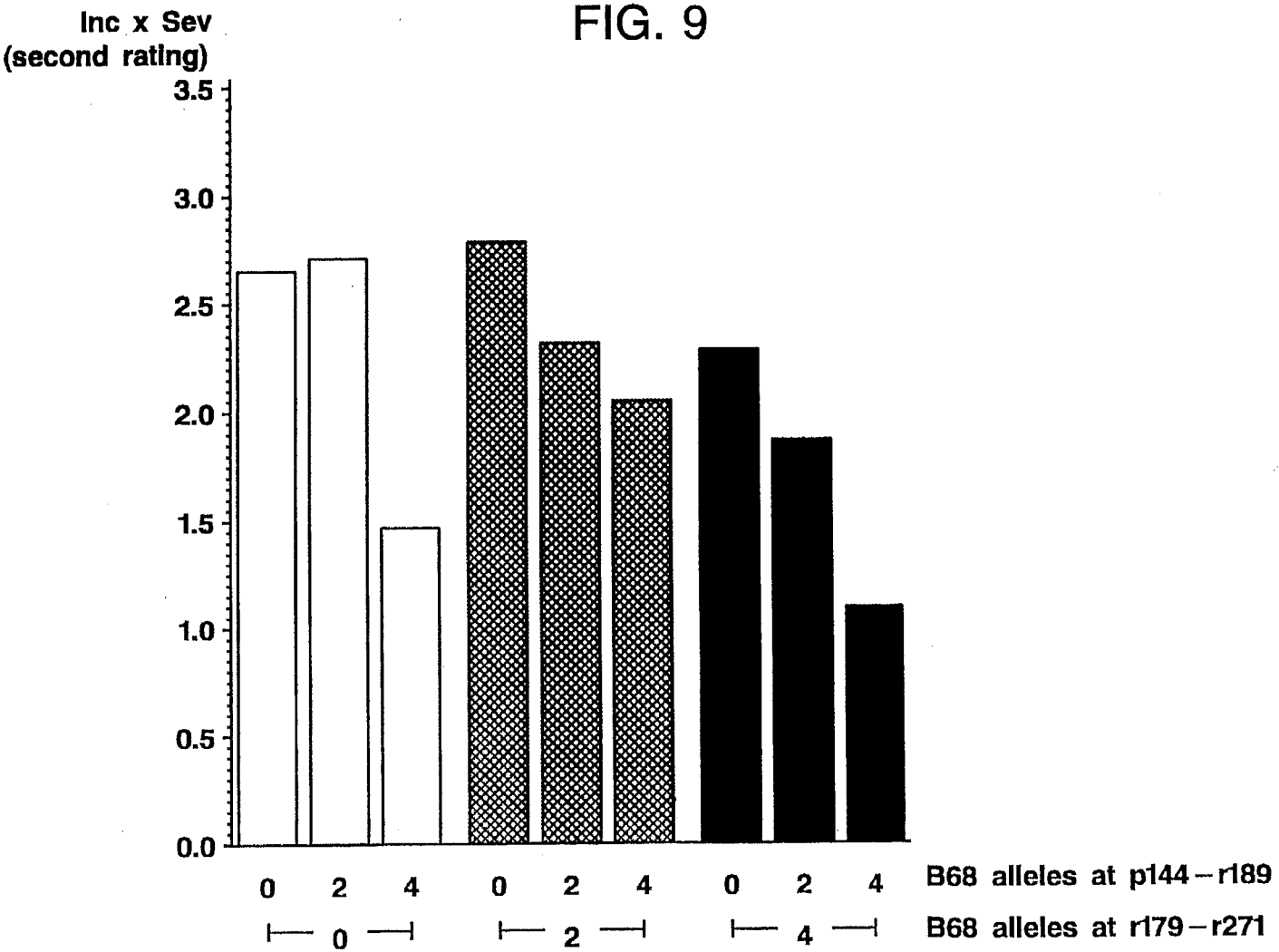
Figure 10:
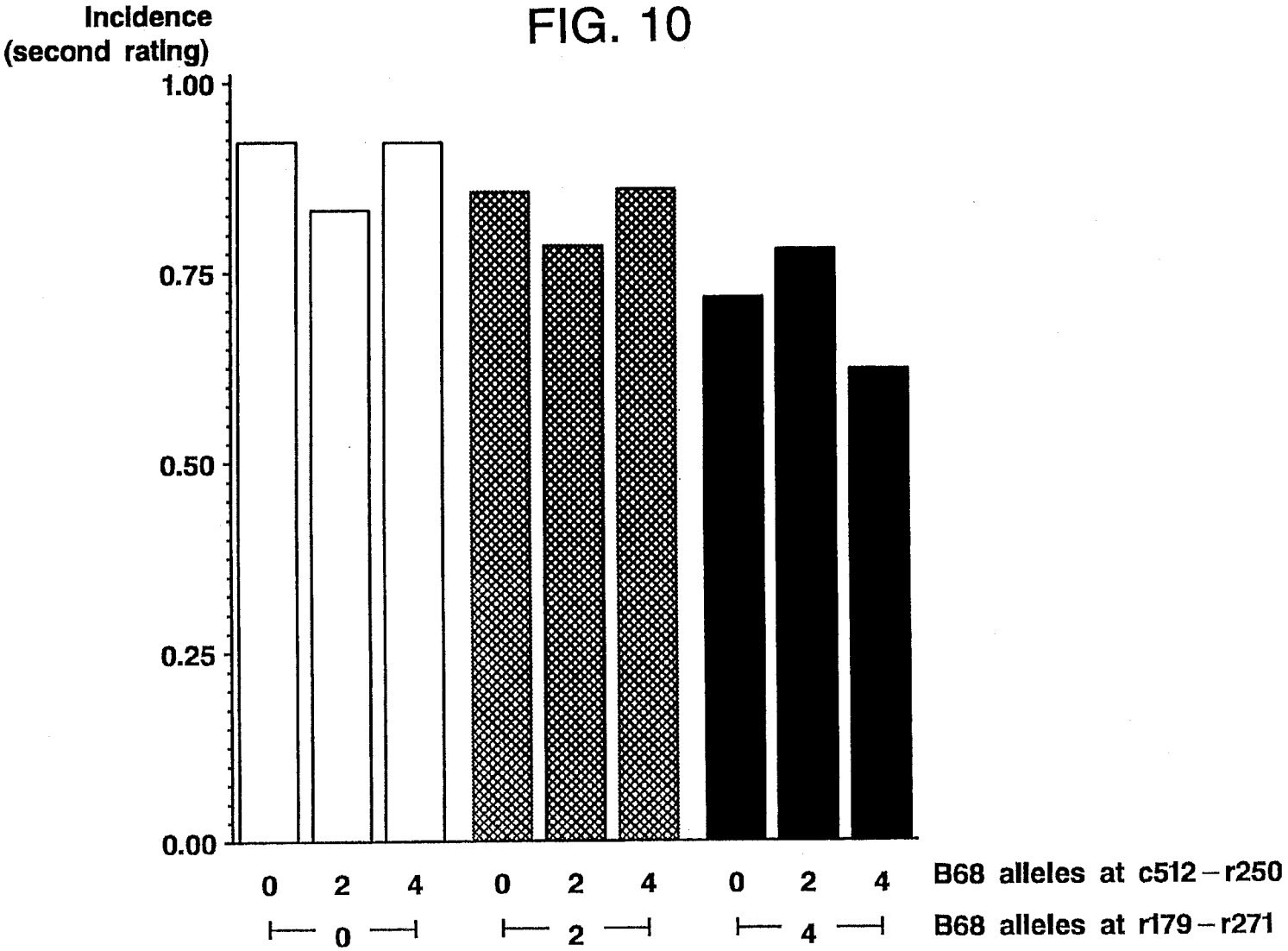
Figure 11:
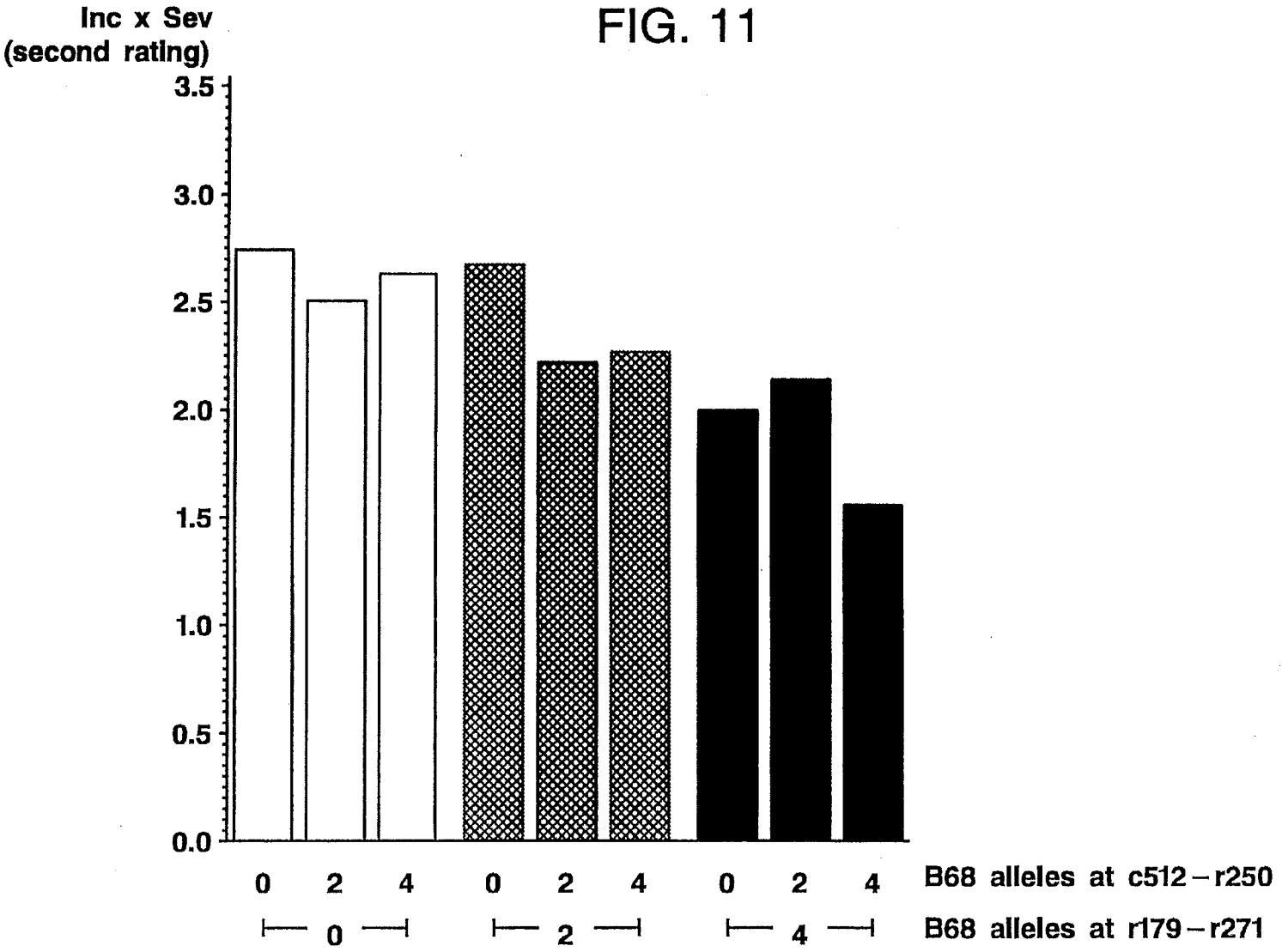
Figure 12:
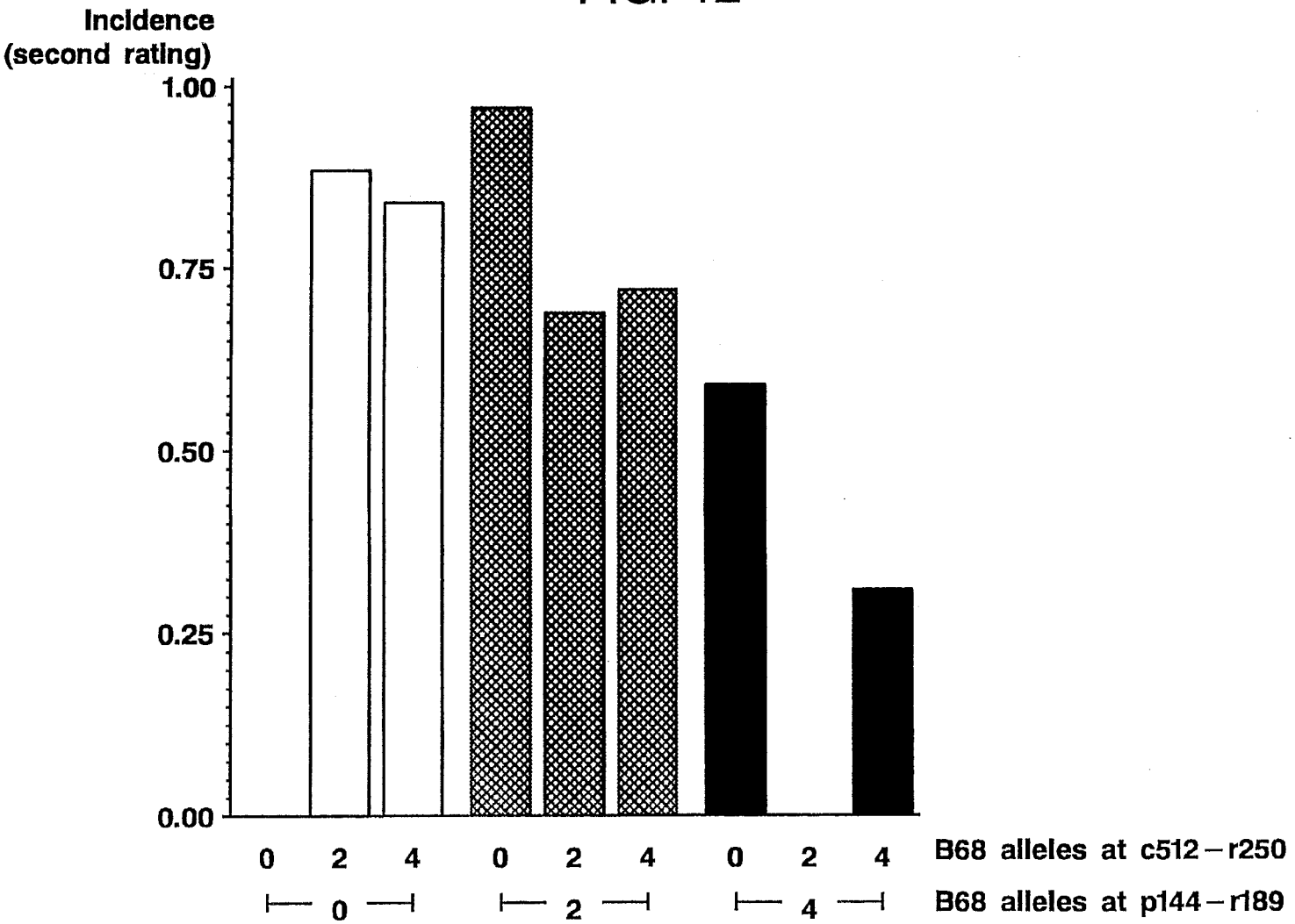
FIG. 12 is a bar chart comparing the effects on MDMV incidence of the number of B68 (MDMV resistant) alleles in chromosome segments B–B1 defined by marker gp144 and r189 and C–C1 defined by marker loci c512 and r250 when segment A–A1 defined by marker loci r179 and r271 is homozygous for B68 alleles to illustrate interaction between said segments.
Figure 13:
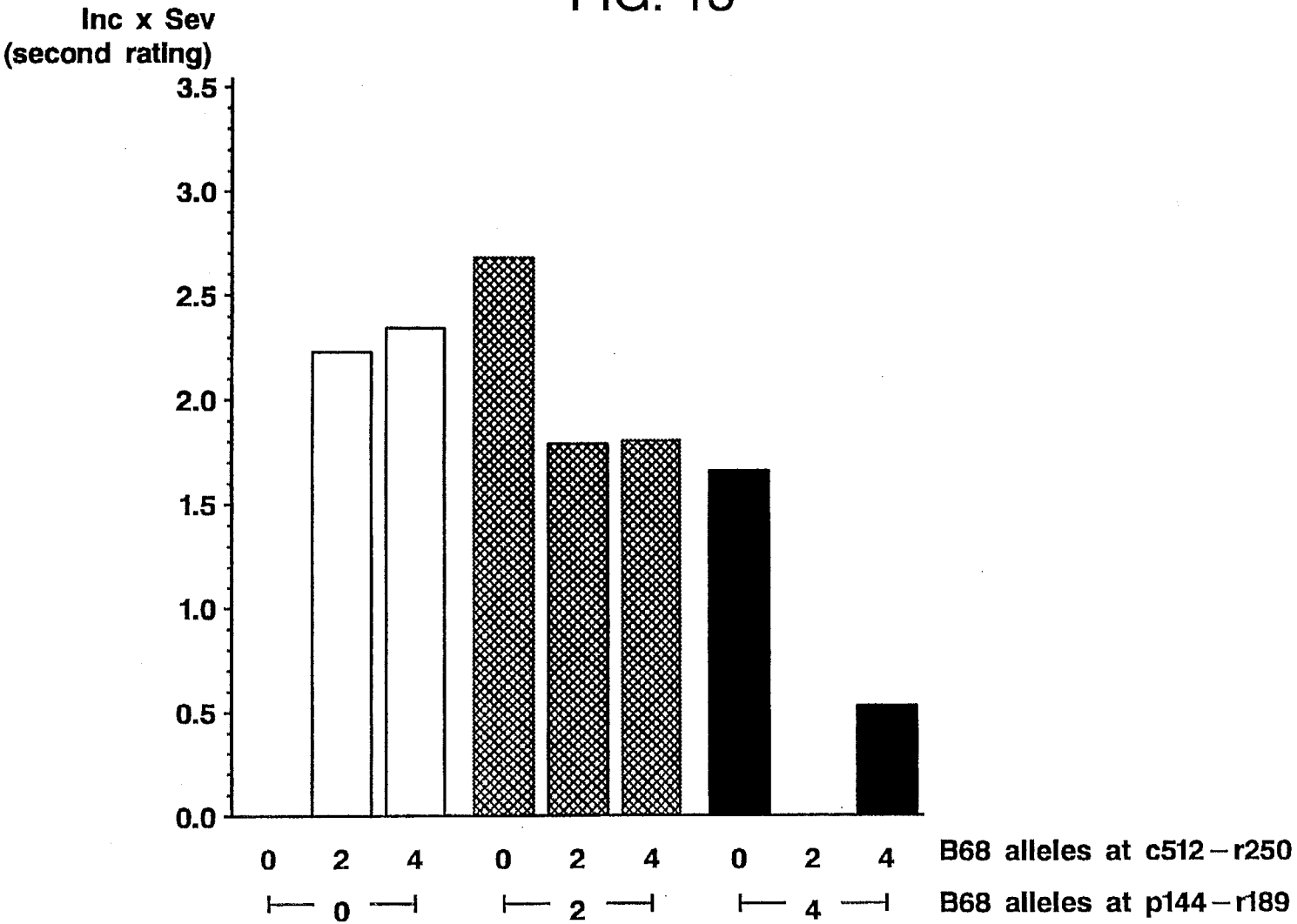
FIG. 13 is a bar chart comparing the effects on MDMV incidence×severity of the number of B68 (MDMV resistant) alleles in the chromosome segments B–B1 defined by marker loci gp144 and r189 and C–C1 defined by marker loci c512 and r250 on MDMV resistance when chromosome segment A–A1 defined by r179 and r271 is homozygous for B68 to illustrate interaction between said segments.

An examination of mean scores for disease by genotype indicated that at least one of the two B68 alleles for r179 must be present for any of the other marker loci, except gp144 to affect resistance (FIGS. 1–7). The marker locus gp144 also appeared to interact with r179, but a mild effect on resistance was seen, even if the B68 morphs for r179 are absent. As the analyses above indicated that the loci of interest probably were within the r179–r271, gp144–r189, and c512–r250 segments, we examined those genotypes which had two B68 alleles for each locus at either end of the segment (4 total) vs. one B68 allele at either end (2 total) vs. no B68 alleles (FIGS. 8, 9). The effect of tracking the r179–r271 segment with the gp144–r189 segment did not dramatically affect the resistance associated with the genotype (compare FIG. 8 with FIG. 1). However, tracking all three segments showed that homozygosity for all three segments was clearly associated with a high level of resistance (FIG. 12). It is also clear that the marker segment r179–r271 is not of itself associated with resistance. Although these data are composed of small numbers of individuals (compare bar charts to data, Table 2), the excellent association between genotype and phenotype indicated that the markers, and marker-bounded segments were potentially useful for the prediction of resistance in S2 progeny. From these analyses we concluded that the first criteria in resistance prediction was the presence of one, and preferably two B68 alleles for the r179 marker locus. Once this criterion was met, then those individuals having the maximum number of B68 alleles for gp144, c512, c329, and r262, respectively, would be expected to be resistant. The ordering of the marker loci was determined by a relative contribution to total $R^2$ values in both I and S data, and apparent magnitude of interaction with r179. We would also expect to see an improvement in the result if marked segments were included, although the effects of recombination could result in resistant individual which were homozygous for the marker locus and heterozygous for the flanking marker.

Example 7

Verification of Prediction

The data from the Lincoln location were not used in the test of the prediction. The disease differential between B73 and B68 (≈0.4–0.5 for I data and ≈1.0 for S data) was lower than expected, and examination of variance between balanced incomplete blocks showed unacceptable differences between disease scores for the same genotype, especially for those genotypes in the moderately susceptible to moderately resistant range. Infection was more severe at Madison and balanced incomplete blocks received similar ratings ($p<0.05$). As in the earlier data, the effect of the time of rating was significant ($p< 0.001$). All four ratings were examined separately.

Multiple regressions of the predictor set on each of the eight sets of ratings showed that although the multiple $r^2$ values were somewhat lower than obtained when the model was fit, the accounting for Y was very good (Table 3). The lower multiple $R^2$ values for incidence were not unexpected because of the absence of marker loci c512 and c587 which were not readable. Examination of the effect of r179 in the 399 S2 progeny clearly confirm that r179 is essential for resistance potential, and supports the results of Mikel et al. Supra in which an epistatic gene was indicated. The effect of the other probes appeared to be primarily

TABLE 3

Multiple Regression Analysis of 7 Marker Loci Predicted to be Involved in Maize Dwarf Mosaic Virus Resistance, and One Flanking Marker (r250) Regression of 399 disease ratings against marker loci

| | Coef | Std Err | t Value |
|---|---|---|---|
| **Regression on first rating for Incidence** | | | |
| r179 | 2.117635e-1 | 0.0638428 | 3.316953 |
| gp144 | 9.547554c-2 | 0.0791312 | 1.206546 |
| r250 | 2.585734e-1 | 0.0365023 | 7.083759 |
| c926 | 1.301470e-4 | 0.0632003 | 0.002059277 |
| c329 | 1.513948e-1 | 0.0456896 | 3.313552 |
| r262 | 1.276097e-1 | 0.0647424 | 1.971037 |
| r92b | 4.639700e-2 | 0.0620268 | 0.7480156 |
| Residual Standard Error = 0.3604575 | | | |
| Multiple R-Square = 0.857966 | | | |
| N = 104 F Value = 83.7051 on 7, 97 df | | | |
| **Regression on second rating for Incidence** | | | |
| r179 | 0.1857877 | 0.06251866 | 2.971716 |
| gp144 | 0.1106930 | 0.07749007 | 1.428480 |
| r250 | 0.2558244 | 0.03574523 | 7.156884 |
| c926 | 0.003455432 | 0.06188958 | 0.0558322 |
| c329 | 0.1632299 | 0.04474197 | 3.648251 |
| r262 | 0.09613084 | 0.06339965 | 1.516267 |
| r92b | 0.07187376 | 0.06074035 | 1.183295 |
| Residual Standard Error = 0.352982 | | | |
| Multiple R-Square = 0.862342 | | | |
| N = 104 F Value = 86.8066 on 7, 97 df | | | |

TABLE 3-continued

Multiple Regression Analysis of 7 Marker Loci Predicted to be Involved in Maize Dwarf Mosaic Virus Resistance, and One Flanking Marker (r250) Regression of 399 disease ratings against marker loci

| | Coef | Std Err | t Value |
|---|---|---|---|
| **Regression on third rating for Incidence** | | | |
| r179 | 0.2437292 | 0.0603624 | 4.037764 |
| gp144 | 0.1212962 | 0.0748175 | 1.621228 |
| r250 | 0.2502463 | 0.0345124 | 7.250910 |
| c926 | 0.01593832 | 0.0597550 | 0.2667276 |
| c329 | 0.1576393 | 0.0431989 | 3.649155 |
| r262 | 0.1028069 | 0.0612130 | 1.679494 |
| r92b | 0.06662901 | 0.0586454 | 1.136132 |
| Residual Standard Error = 0.3408075 | | | |
| Multiple R-Square = 0.882785 | | | |
| N = 104 F Value = 104.3624 on 7, 97 df | | | |
| **Regression on fourth rating for Incidence** | | | |
| r179 | 0.2937771 | 0.04858226 | 6.047005 |
| gp144 | 0.1449855 | 0.06021630 | 2.407746 |
| r250 | 0.1887696 | 0.02777705 | 6.795886 |
| c926 | 0.03259441 | 0.04809340 | 0.677731 |
| c329 | 0.09876792 | 0.03476828 | 2.840748 |
| r262 | 0.08933747 | 0.04926686 | 1.813338 |
| r92b | 0.1141951 | 0.04720036 | 2.419369 |
| Residual Standard Error = 0.2742964 | | | |
| Multiple R-Square = 0.914860 | | | |
| N = 104 F Value = 148.9006 on 7, 97 df | | | |
| **Regression on first rating for Incidence × Severity** | | | |
| r179 | 0.4174503 | 0.0734569 | 5.682928 |
| gp144 | 0.1732581 | 0.0910477 | 1.902938 |
| r250 | 0.2143294 | 0.0419992 | 5.103179 |
| c926 | 0.04433341 | 0.0727177 | 0.6096642 |
| c329 | 0.1473353 | 0.0525700 | 2.802649 |
| r262 | 0.1932943 | 0.0744920 | 2.594832 |
| r92b | 0.02681083 | 0.0713674 | 0.3756731 |
| Residual Standard Error = 0.4147391 | | | |
| Multiple R-Square = 0.879232 | | | |
| N = 104 F Value 100.8846 on 7, 97 df | | | |
| **Regression on second rating for Incidence × Severity** | | | |
| r179 | 0.3969871 | 0.0863667 | 4.596527 |
| gp144 | 0.2423920 | 0.1070491 | 2.264307 |
| r250 | 0.2462625 | 0.0493804 | 4.987045 |
| c926 | 0.0657849 | 0.0854977 | 0.769435 |
| c329 | 0.1838871 | 0.0618090 | 2.975083 |
| r262 | 0.1955799 | 0.0873838 | 2.233060 |
| r92b | 0.1768786 | 0.0839101 | 2.107954 |
| Residual Standard Error = 0.4876284 | | | |
| Multiple R-Square = 0.888229 | | | |
| N = 104 F Value = 110.1209 on 7, 97 df | | | |
| **Regression on third rating for Incidence × Severity** | | | |
| r179 | 0.5092413 | 0.07231843 | 7.041653 |
| gp144 | 0.2694907 | 0.08963659 | 3.006481 |
| r250 | 0.1928990 | 0.04134828 | 4.665225 |
| c926 | 0.0751274 | 0.07159073 | 1.049401 |
| c329 | 0.1621395 | 0.05175526 | 3.132813 |
| r262 | 0.1660191 | 0.07333751 | 2.263767 |
| r92b | 0.1482765 | 0.07026136 | 2.110357 |
| Residual Standard Error = 0.4083113 | | | |
| Multiple R-Square = 0.917977 | | | |
| N = 104 F Value = 155.0855 on 7, 97 df | | | |
| **Regression on fourth rating for Incidence × Severity** | | | |
| r179 | 0.5464476 | 0.06342066 | 8.616237 |
| gp144 | 0.2575648 | 0.07860808 | 3.276569 |
| r250 | 0.1329957 | 0.03626096 | 3.667739 |
| c926 | 0.1278032 | 0.06278250 | 2.035650 |
| c329 | 0.1037226 | 0.04538751 | 2.285267 |
| r262 | 0.1340554 | 0.06431437 | 2.084378 |
| r92b | 0.2208268 | 0.06161670 | 3.583878 |
| Residual Standard Error = 0.3580744 | | | |

TABLE 3-continued

| Multiple Regression Analysis of 7 Marker Loci Predicted to be Involved in Maize Dwarf Mosaic Virus Resistance, and One Flanking Marker (r250) Regression of 399 disease ratings against marker loci | | |
|---|---|---|
| Coef | Std Err | t Value |
| Multiple R-Square = 0.9334<br>N = 104 F Value = 194.2056 on 7, 97 df | | |

The flanking marker to p512 is r250 (3.8 mu from c512 on side opposite to c587)

additive, as predicted, when the r179 marker locus has at least one, and preferably two B68 alleles.

We claim:

1. A nucleic acid probe designated gp144.

* * * * *